United States Patent
Konishi

(10) Patent No.: US 9,174,894 B2
(45) Date of Patent: Nov. 3, 2015

(54) METHOD FOR PRODUCING CYCLOOLEFIN AND PRODUCTION APPARATUS THEREOF

(75) Inventor: Mitsuo Konishi, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 839 days.

(21) Appl. No.: 13/055,103

(22) PCT Filed: Jun. 12, 2009

(86) PCT No.: PCT/JP2009/060761
§ 371 (c)(1),
(2), (4) Date: Jan. 20, 2011

(87) PCT Pub. No.: WO2010/013548
PCT Pub. Date: Apr. 2, 2010

(65) Prior Publication Data
US 2011/0130600 A1    Jun. 2, 2011

(30) Foreign Application Priority Data

Jul. 30, 2008   (JP) .................................. 2008-196265

(51) Int. Cl.
*C07C 5/11* (2006.01)
*B01J 8/00* (2006.01)
(Continued)

(52) U.S. Cl.
CPC . *C07C 5/11* (2013.01); *B01J 23/96* (2013.01); *B01J 38/70* (2013.01); *B01J 23/462* (2013.01); *C07C 2523/46* (2013.01)

(58) Field of Classification Search
USPC ........................................................ 585/254
See application file for complete search history.

(56) References Cited

U.S. PATENT DOCUMENTS

| 6,077,983 A | 6/2000 | Ono et al. |
| 2007/0298960 A1* | 12/2007 | Poole et al. ..................... 502/12 |
| 2009/0048425 A1* | 2/2009 | Konishi et al. ................ 528/396 |

FOREIGN PATENT DOCUMENTS

| CN | 1105964 A | 8/1995 |
| CN | 1107757 A | 9/1995 |

(Continued)

OTHER PUBLICATIONS

Machine translated English document of JP2925129.*

(Continued)

*Primary Examiner* — In Suk Bullock
*Assistant Examiner* — Youngsul Jeong
(74) *Attorney, Agent, or Firm* — Finnegan, Henderson, Farabow, Garrett & Dunner, L.L.P.

(57) ABSTRACT

There is provided a method for producing cycloolefin where the nickel which elutes in the liquid-contact portion of the reactor is removed from the reaction system of the partial hydrogenation reaction and cycloolefin can be stably produced from a monocyclic aromatic hydrocarbon over a long term. A method for producing a cycloolefin by a partial hydrogenation reaction of a monocyclic aromatic hydrocarbon in an aqueous phase, which contains a metal salt-containing acidic aqueous solution and a ruthenium catalyst in a reactor with a liquid-contact portion formed of a nickel-containing material, the method comprising a first step of bringing at least a part of the ruthenium catalyst contained in the aqueous phase into contact with oxygen, a second step of separating the aqueous phase containing the ruthenium catalyst that has been processed in the first step into a first phase containing the ruthenium catalyst at a high ratio and a second phase containing the ruthenium catalyst at a lower ratio than the first phase, and a third step of feeding the first phase to a reaction system of a partial hydrogenation reaction.

6 Claims, 2 Drawing Sheets

(51) Int. Cl.
    *B01J 23/96*     (2006.01)
    *B01J 38/70*     (2006.01)
    *B01J 23/46*     (2006.01)

(56) References Cited

FOREIGN PATENT DOCUMENTS

| | | | |
|---|---|---|---|
| EP | 1488015 B1 | * | 12/2004 |
| JP | 01-159059 | | 6/1986 |
| JP | 03-068453 | | 3/1991 |
| JP | 07-165621 | | 6/1995 |
| JP | 07-227542 | | 8/1995 |
| JP | 2634828 | | 4/1997 |
| JP | 2886563 | | 2/1999 |
| JP | 2925129 | | 5/1999 |
| JP | 2925129 | * | 7/1999 |
| JP | 2001-026556 | | 1/2001 |
| JP | 2004-315380 | | 11/2004 |
| WO | WO 97/16249 A1 | | 5/1997 |
| WO | WO 2007/023739 A1 | | 3/2007 |
| WO | WO 2007023739 A1 | * | 3/2007 |

OTHER PUBLICATIONS

Lin et al., Photocatalytic removal of nickel from aqueous solutions from untraviolet-irradiated TiO2, 1997, J. Electrochem. Soc., vol. 144, No. 8, pp. 2751-2756.*

Pirkanniemi et al., 2002, Heterogeneous water phase catalysis as an environmental application: a review, Chemosphere, vol. 48, pp. 1047-1060.*

International Search Report from the Japanese Patent Office for International Application No. PCT/JP2009/060761, mailing date Aug. 18, 2009.

International Preliminary Report on Patentability dated Mar. 17, 2011 issued in PCT/JP2009/060761.

Office Action for JP Applicaiton No. 2010-522657 mailed Jan. 10, 2013.

Office Action for TW Application No. 098124467 mailed Sep. 28, 2012.

Office Action for CN Application No. 200980129802.X mailed Jan. 24, 2013.

* cited by examiner

METHOD FOR PRODUCING CYCLOOLEFIN AND PRODUCTION APPARATUS THEREOF

TECHNICAL FIELD

The present invention relates to a method for producing cycloolefin by partially hydrogenating a monocyclic aromatic hydrocarbon and a production apparatus thereof.

BACKGROUND ART

Conventionally, various methods for producing cycloolefin have been known. Among them, a method for partially hydrogenating a monocyclic aromatic hydrocarbon using a ruthenium catalyst in liquid phase is most typical. Furthermore, many results of investigations into catalyst components, types of carriers, metal salts as additives to the reaction system, or the like have been reported as methods for increasing selectivity or yield of cycloolefin when the cycloolefin is produced.

In an apparatuses used when cycloolefin is produced by such a method, material corrosion progresses in the portion (hereinafter, referred to as liquid-contact portion) where liquid contacts a reactor or the like by anion and/or alkali as additives. As a result, it has been known that there occurs a phenomenon where activity and/or selectivity of catalysts are/is reduced by a metallic component which elutes from the liquid-contact portion, or the like. Thus, as materials of the liquid-contact portion in a reactor or the like, there are proposed means using a nickel group alloy containing molybdenum or a nickel group alloy containing chromium and molybdenum with a slow metal elution rate (Patent Document 1). Furthermore, in Patent Document 1, there are proposed a method where a reaction was performed by maintaining a concentration of nickel in an aqueous phase of a reaction liquid at 50 ppm or less. Furthermore, there is proposed a method of controlling an operation in this range where a ratio of a total amount of metals which elutes from a hydrogenation reactor and a heat exchange system to a total mass of a hydrogenation catalyst does not exceed 0.5% by mass (Patent Document 2).

As a method for regenerating a ruthenium catalyst whose activity has decreased due to an interaction between hydrogen and the ruthenium catalyst, there is proposed a method of bringing the ruthenium catalyst into contact with oxygen in a liquid phase (Patent Document 3). Furthermore, there is proposed a method of maintaining the ruthenium catalyst in a liquid phase at a hydrogen partial pressure lower than that at a hydrogenation reaction condition and at a temperature within a range from a temperature not lower than a temperature lower by 50° C. than that at the hydrogenation reaction condition to 250° C. (Patent Document 4).

There is proposed a method of restoring an activity of the ruthenium catalyst including steps of bringing the ruthenium catalyst into contact with oxygen in a liquid phase and maintaining the catalyst at a hydrogen partial pressure lower than that at a hydrogenation reaction and at a temperature not lower than a temperature lower by 50° C. than temperature of the hydrogenation reaction (Patent Document 5).
Patent Document 1: Japanese Patent No. 2925129
Patent Document 2: Japanese Patent Application Laid-Open No. 2004-315380
Patent Document 3: Japanese Patent No. 2634828
Patent Document 4: Japanese Patent No. 2886563
Patent Document 5: International Publication No. 97/16429

SUMMARY OF THE INVENTION

Problems to be Solved by the Invention

However, all the above-mentioned methods of treating deterioration of the catalytic performance due to metals such as nickel which elute from a reactor have certain problems from the view point of industrial long-term use in years of a hydrogenation catalyst, and thus it cannot be said that they are industrially advantageous. An industrial production apparatus of cycloolefin has a large liquid-contact area of the member. Thus, as the method described in Patent Document 1, even though the materials of the liquid-contact portion in the hydrogenation reactor and/or the concentration of nickel of the reaction liquid in aqueous phase are/is controlled, when the hydrogenation catalyst is used over a long term of several years, the catalytic performance is remarkably deteriorated. As a result, it is necessary to frequently exchange the catalyst.

Furthermore, as described in Patent Document 2, the method of controlling the operation in this range where the ratio of the total amount of the metals which elute from the hydrogenation reactor and the heat exchange system to the total mass of the hydrogenation catalyst does not exceed 0.5% by mass, is effective from the viewpoint of stably producing cycloolefin. When HASTELLOY B (trade name, heat resistance nickel alloy produced by Haynes stellite Co.) described in Examples thereof is used in materials of a hydrogenation reactor, or the like, the catalyst can be continuously used over a long term of several years. However, at present, HASTELLOY B is difficult to obtain. Furthermore, there is HASTELLOY C (trade name, heat resistance nickel alloy produced by Haynes stellite Co.) as a material similar to HASTELLOY B. However, according to a study of the present inventor, since HASTELLOY C has an elution rate of metal higher than that of HASTELLOY B, the catalyst cannot be continuously used for several years. As a result, it has been found that it is necessary to frequently exchange the catalyst. On the other hand, as described in Patent Document 3, the method of regenerating the hydrogenation catalyst by bringing the ruthenium catalyst into contact with oxygen in the liquid phase is considerably effective in regenerating the deteriorated catalyst due to interaction between hydrogen and the ruthenium catalyst. However, the method is not effective in regenerating the hydrogenation catalyst with the deteriorated performance due to nickel which elutes from the liquid-contact portion of the reactor, or the like. Furthermore, regarding the method of maintaining the ruthenium catalyst in the liquid phase at the hydrogen partial pressure lower than that at the hydrogenation reaction condition and at the temperature within the range from the temperature not lower than the temperature lower by 50° C. than that at the hydrogenation reaction condition to 250° C. described in Patent Document 4, the method is not effective in regenerating the hydrogenation catalyst with the deteriorated performance due to nickel or the like. The method described in Patent Document 5 is also not effective.

As clear from the above-mentioned description, conventionally, there is no industrially effective method of restoring performance of the hydrogenation catalyst deteriorated by the elution of nickel and the catalyst has to be exchanged.

The invention has been made in view of these circumstances, and an object of the invention is to provide a method for producing cycloolefin where cycloolefin can be stably produced over a long term by removing nickel which elutes from the liquid-contact portion of the reactor, from a reaction system of a partial hydrogenation reaction, and a production apparatus thereof.

Means for Solving the Problems

As a result of the present inventor's study with regard to restoring the performance of the hydrogenation catalyst, it has been found that nickel which elutes from the liquid-contact portion of the reactor or the like is present on the ruthenium catalyst. Surprisingly, the inventor has found that the aqueous phase containing the ruthenium catalyst where the eluted metal is present is brought into contact with oxygen, and thereby nickel is desorbed from the ruthenium catalyst to be dissolved in the aqueous solution. On the basis of these facts, the inventor has conceived a treatment where the aqueous phase containing the ruthenium catalyst is brought into contact with oxygen, then slurry containing the ruthenium catalyst of the aqueous phase is separated from a supernatant dissolving nickel, and the slurry containing the ruthenium catalyst is fed into the reaction system of the partial hydrogenation reaction. The inventor found that an amount of nickel to the ruthenium catalyst can be controlled not to increase in the reaction system of the partial hydrogenation reaction by a treatment where the supernatant dissolving nickel is discharged outside the system, and reduction of the catalytic performance can be suppressed over a long term, and thus realized the present invention.

Furthermore, inorganic salt such as zinc is contained in the supernatant separated as described above, thus when the supernatant is discarded, cumbersome operations of neutralization, precipitation treatments, or the like of the supernatant are required. As a result of the inventor intensive's study, it has been found that supernatant dissolving nickel is brought into contact with a metal catalyst, whereby the concentration of nickel in the supernatant is reduced. It has been found that the supernatant after the contact with the metal catalyst is added into the aqueous phase containing the ruthenium catalyst again, whereby the separated supernatant does not have to discarded, and further the amount of nickel to the ruthenium catalyst is controlled not to increase in the hydrogenation reaction system, and reduction of the catalytic performance is suppressed over a long term.

In other words, the present invention is as follows.

[1] A method for producing a cycloolefin by a partial hydrogenation reaction of a monocyclic aromatic hydrocarbon in an aqueous phase which contains a metal salt-containing acidic aqueous solution and a ruthenium catalyst, in a reactor with a liquid-contact portion formed of a nickel-containing material, the method including a first step of bringing at least a part of the ruthenium catalyst contained in the aqueous phase into contact with oxygen, a second step of separating the aqueous phase containing the ruthenium catalyst that has been processed in the first step into a first phase containing the ruthenium catalyst at a high ratio and a second phase containing the ruthenium catalyst at a lower ratio than the first phase, and a third step of feeding the first phase to a reaction system of the partial hydrogenation reaction.

[2] The method for producing the cycloolefin according to [1], further including a sixth step of feeding a metal salt-containing acidic aqueous solution including nickel by an amount lower than an amount of nickel contained in the second phase to the reaction system of the partial hydrogenation reaction.

[3] The method for producing the cycloolefin according to [2], further including a fourth step of bringing the second phase into contact with a metal catalyst, wherein in the sixth step, the second phase that has been processed in the fourth step is fed to the reaction system of the partial hydrogenation reaction as the metal salt-containing acidic aqueous solution including the nickel.

[4] The method for producing the cycloolefin according to [3], wherein in the fourth step, the second phase is brought into contact with the metal catalyst under the atmosphere containing hydrogen.

[5] The method for producing the cycloolefin according to [3] or [4], further including a fifth step of bringing the metal catalyst that has been processed in the fourth step into contact with an acidic solution.

[6] The method for producing the cycloolefin according to any one of [3] to [5], wherein the metal catalyst contains at least one kinds of metal selected from the group consisting of Cu, Ag, Au, Pd, Pt, Rh, Ir, Ru and Re.

[7] The method for producing the cycloolefin according to any one of [1] to [6], wherein the metal salt contains zinc sulfate.

[8] The method for producing the cycloolefin according to any one of [1] to [7], wherein a sum of a total mass of nickel present on the ruthenium catalyst and a total mass of nickel in the metal salt-containing acidic aqueous solution is controlled not to exceed 5% by mass based on a total mass of ruthenium in the ruthenium catalyst.

[9] A production apparatus of a cycloolefin including a reactor, an oil/water separation tank connected to the reactor, an oxygen treatment equipment connected to the oil/water separation tank, and a catalyst separation tank connected to the oxygen treatment equipment, wherein the reactor is a reactor to accommodate an aqueous phase which contains a metal salt-containing acidic aqueous solution and a ruthenium catalyst, and a partial hydrogenation reaction of a monocyclic aromatic hydrocarbon is processed in the aqueous phase, thereby obtaining an oil phase comprising an unreacted monocyclic aromatic hydrocarbon and a reaction product is obtained; the oil/water separation tank is a tank to separate at least a part of the oil phase, and at least a part of the aqueous phase containing the ruthenium catalyst, wherein the oil phase and the aqueous phase have been processed in the reactor and fed to the tank; the oxygen treatment equipment is an equipment to bring at least a part of the ruthenium catalyst contained in the aqueous phase that has been processed in the oil/water separation tank and fed thereto, into contact with oxygen; and the catalyst separation tank is a tank to separate the aqueous phase containing the ruthenium catalyst that has been processed in the oxygen treatment equipment and fed thereto, into a first phase containing the ruthenium catalyst at a high ratio and a second phase containing the ruthenium catalyst at a lower ratio than the first phase, and the catalyst separation tank is connected such that the first phase is fed to the reactor.

[10] The production apparatus of the cycloolefin according to [9], further including an oil stripping tank which connects the oil/water separation tank and the oxygen treatment equipment, wherein the oil stripping tank is a tank to remove at least a part of the oil phase contained in the aqueous phase that has been processed in the oil/water separation tank and fed thereto, from the aqueous phase.

[11] The production apparatus of the cycloolefin according to [9] or [10], further including a nickel removal equipment connected to the catalyst separation tank, wherein the nickel removal equipment is an equipment to remove at least a part of nickel from the second phase that has been processed in the catalyst separation tank and fed thereto.

[12] The production apparatus of the cycloolefin according to any one of [9] to [11], further including a low hydrogen partial pressure treatment equipment which connects to the catalyst separation tank and the oxygen treatment equipment, wherein the low hydrogen partial pressure treatment equipment is an equipment to maintain the ruthenium catalyst under an atmosphere of a hydrogen partial pressure lower than a hydrogen partial pressure at the partial hydrogenation reaction.

Advantages of the Invention

The invention can remove nickel which elutes from the liquid-contact portion of the reactor, from the reaction system of the partial hydrogenation reaction, thus producing a cycloolefin from monocyclic aromatic hydrocarbons stably over a long term can be achieved.

MODE FOR CARRYING OUT THE INVENTION

Figure 1:
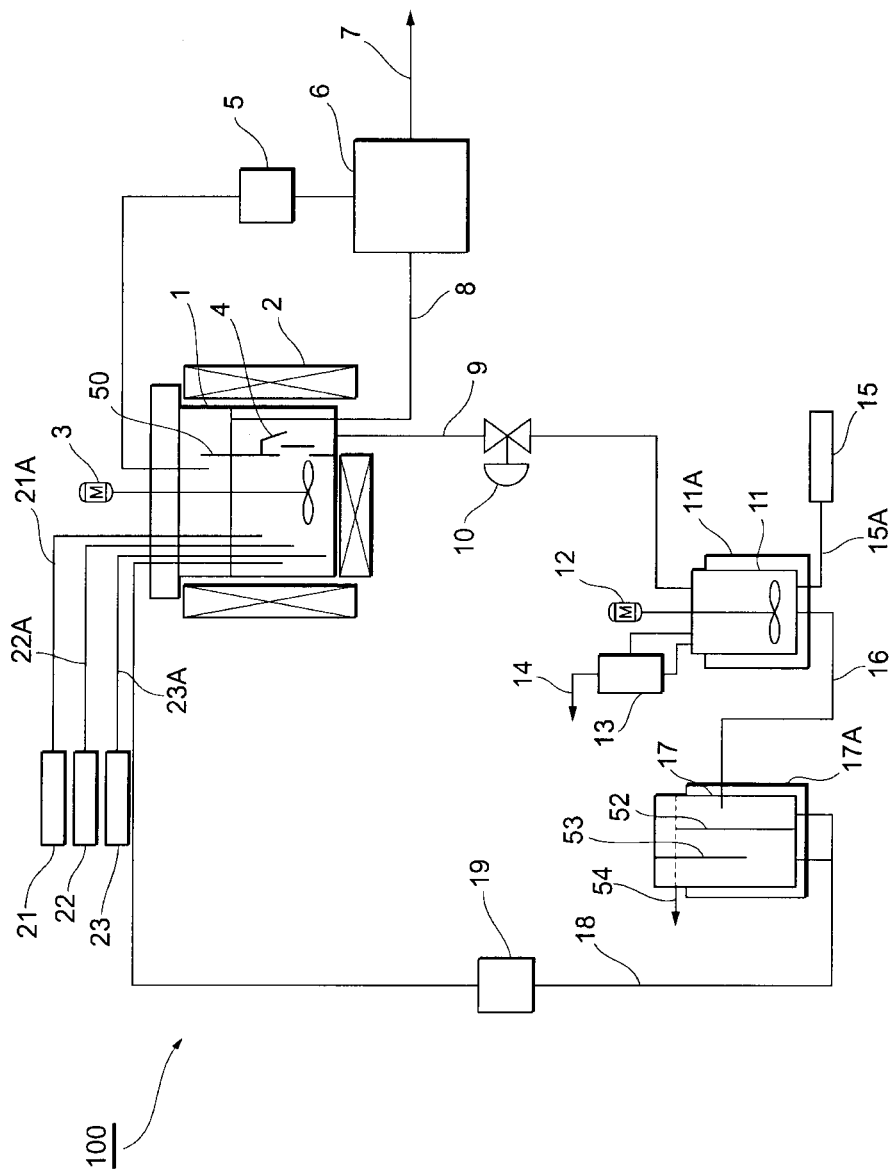
FIG. 1 shows a schematic diagram illustrating a production apparatus of cycloolefin according to one example of the invention.

Hereinafter, an embodiment for carrying out the present invention (hereinafter referred to as "the present embodiment") will be described, while the invention refers to figures as necessary. However, the present invention is not limited to the following embodiment. Various modifications can be made without departing from the spirit of the present invention. Further, in figures, the same numerals are assigned to the same elements, and the overlapping description will be omitted. Furthermore, dimensional ratio of figures is not limited to the ratio shown in figures.

[1] Method for Producing of Cycloolefin

In a method for producing a cycloolefin of the present embodiment, the cycloolefin is produced by the partial hydrogenation reaction of a monocyclic aromatic hydrocarbon in an aqueous phase which contains a ruthenium catalyst and an acidic aqueous solution (hereinafter, referred to as "metal salt aqueous solution") containing a metal salt in a reactor with liquid-contact portion formed of a material (hereinafter, referred to as "nickel-containing material") containing nickel. The method comprises (1) a first step of bringing at least a part of the ruthenium catalyst contained in the aqueous phase into contact with oxygen, (2) a second step of separating the aqueous phase containing the ruthenium catalyst that has been processed in the first step into a first phase containing the ruthenium catalyst at a high ratio and a second phase containing the ruthenium catalyst at a lower ratio than the first phase, and (3) a third step of feeding the first phase to a reaction system of the partial hydrogenation reaction.

(1) Partial Hydrogenation Reaction (a) Starting Material

Examples of the monocyclic aromatic hydrocarbons used as the starting material of the partial hydrogenation reaction in the present embodiment include alkylbenzene having a low alkyl group of 1 to 4 carbon atoms such as toluene and xylene, other than benzene.

Water is required in the partial hydrogenation reaction, and the amount thereof depends on the reaction type. The amount of water is preferably 0.5 to 20 times on a mass basis with respect to an amount of the monocyclic aromatic hydrocarbon as the starting material. When the amount of water is within this range, there is a tendency that cycloolefin selectivity can be maintained without increasing the size of the reactor. More preferably, the amount of water is 1 to 10 times on a mass basis with respect to the monocyclic aromatic hydrocarbon as the starting materials. In any case, it is necessary that water is present in the reaction system in an amount enough to form a state in which a reaction liquid phase (an organic substance liquid phase, hereinafter, referred to as "oil phase") containing a starting material, that is, the monocyclic aromatic hydrocarbon or a reaction product (for example, cycloolefin) as a main component is phase-separated from a aqueous phase containing water as a main component, that is, the two-liquid-phase state composed of the oil phase and the aqueous phase. A pH of the metal salt aqueous solution contained in the aqueous phase is acidic with a value of less than 7.0. More preferably, the pH is 2 to 6.5.

(b) Metal Salt

It is necessary that a metal salt is present in the reaction system. The metal salt is preferably present in the aqueous phase in a state where at least a part or all of the same is dissolved therein. Examples of metals formed of the metal salt include zinc, iron, cadmium, gallium, indium, aluminum, chromium, manganese, cobalt and copper. Furthermore, examples of these metal salts include nitrate, acetate, phosphate, and sulfate of the metals. These metal salts may be a double salt containing these metal salts. These metal salts may be used alone or combination of two or more kinds. From the viewpoint of improvement of cycloolefin yield, zinc sulfate is preferably used as the metal salt. A concentration of the metal salt in the aqueous phase is preferably from $1 \times 10^{-5}$ to 5.0 mol/L. When a metal salt containing zinc sulfate is used, the concentration of the metal salt in the aqueous phase is preferably from $1 \times 10^{-3}$ to 2.0 mol/L, and more preferably from 0.1 to 1.0 mol/L.

In addition, the following metal salts may be present in the reaction system. Examples of the metals formed of the metal salts include group 1 metals in the periodic table such as lithium, sodium and potassium, group 2 metals in the periodic table such as magnesium and calcium (the group numbers are in accordance with the notation of a revised edition (1989) of IUPAC Inorganic Chemistry Nomenclature), and metals such as lead, arsenic, germanium, vanadium, silver, gold, platinum, palladium, barium, and boron. Furthermore, examples of the metal salts thereof include nitrates, oxides, hydroxides, acetates, phosphates, or one where two or more of these metal salts may be chemically or physically mixed. Among them, zinc salts such as zinc hydroxide and zinc oxide are preferred from the viewpoint of stabilizing the catalytic performance. Particularly preferred are double salts containing zinc hydroxide. For example, the double salts are preferably, a double salt (m:n=1:0.01~100) represented by the general formula: $(ZnSO_4)_m \cdot (Zn(OH)_2)_n$. An amount of the metal salt is not specifically limited in the reaction system so long as the acidity is maintained in aqueous phase. However, the amount of the metal salt is usually in this range of from $1 \times 10^{-5}$ to $1 \times 10^5$ times on a mass basis with respect to the amount of ruthenium in the ruthenium catalyst. The metal salt may be present anywhere in the reaction system, and all of the metal salt is not necessarily dissolved in the aqueous phase with respect to the form. The metal salt may be present in the oil phase, and a part of the metal salt in the aqueous phase or the oil phase may be precipitated.

Furthermore, in order that the acidity is maintained in the aqueous phase, general acid, for example, nitric acid, sulfuric acid, acetic acid, phosphoric acid, or the like may be contained in the reaction system. In particular, the sulfuric acid is considerably effective for increasing reaction velocity, and thus it is preferred.

(c) Ruthenium Catalyst

The ruthenium catalyst may contain ruthenium as active species of the partial hydrogenation reaction, and is preferably the one which contains metallic ruthenium obtained by reducing various ruthenium compounds in advance. The ruthenium compounds include, for example, halides such as chlorides, bromides and iodides, or nitrates, sulfates, hydroxides, of ruthenium, or various complexes containing ruthenium and compounds derived from these complexes. The complexes containing ruthenium include, for example, a ruthenium carbonyl complex, a ruthenium acetylacetonate complex, a ruthenocene complex, a ruthenium ammine complex and a ruthenium hydride complex. These ruthenium compounds can be used alone or in combination of two or more.

A method for reducing these ruthenium compounds includes a catalytic reduction method with hydrogen, carbon monoxide or the like, or a chemical reduction method with formalin, sodium borohydride, potassium borohydride, hydrazine or the like. Among them, the catalytic reduction method with hydrogen and the chemical reduction method with sodium borohydride are preferred. In the case of the catalytic reduction with hydrogen, the ruthenium compounds are reduced and activated generally at a reduction temperature of from 50 to 450° C., preferably from 100 to 400° C. When the reduction temperature is lower than 50° C., the reduction takes too much time for the reduction, and when it is higher than 450° C., aggregation of ruthenium may proceed, resulting in adverse effects on the ruthenium catalyst activity and selectivity. The reduction may be carried out in a gas phase or a liquid phase, preferably in the liquid phase. Further, in the case of the chemical reduction method with sodium borohydride, the reduction temperature is preferably 100° C. or lower, more preferably from 10 to 60° C.

After the ruthenium catalyst is charged into a reactor, the reduction may be performed. In other words, a ruthenium compound which does not contain metallic ruthenium is charged into the reactor as a precursor of the ruthenium catalyst. The ruthenium compound which does not contain metallic ruthenium is preferably used in the form of a ruthenium hydroxide on a carrier obtained by loading the ruthenium compound as described above on a carrier and treating the product with an alkali such as sodium hydroxide. Alternatively, the ruthenium compound which does not contain metallic ruthenium is preferably a mixture of ruthenium hydroxide and a dispersant which is obtained by adding an alkali such as sodium hydroxide to a mixture containing the dispersant and the above ruthenium compound. There is a case where the ruthenium compounds contain an anion such as chloride ion, which may promote the material corrosion, but the anion can be prevented from entering into a reaction system by treating the ruthenium compounds with alkali.

Furthermore, the ruthenium catalyst may be one obtained by adding, to the ruthenium compound before, during or after reduction, other metals and/or metal compounds, for example, zinc, chromium, molybdenum, tungsten, manganese, cobalt, iron, copper, gold, platinum, boron, lanthanum, cerium and/or compounds of these metals. When these metals or metal compounds are added, an amount of metal and/or metal compound as an atomic ratio of the metal to the ruthenium atom is generally in this range of from 0.001 to 20. Among the metals or metal compounds as described above, zinc and/or a zinc compound is preferred. Zinc and/or a zinc compound is preferably added before or during the reduction of the ruthenium compound, and an additive amount of zinc and/or a zinc compound is preferably in this range of from 0.1 to 50 parts by mass of zinc based on 100 parts by mass of ruthenium. Further, from the viewpoint of catalytic activity and cycloolefin selectivity, the additive amount is most preferably in this range of from 0.5 to 30 parts by mass of zinc based on 100 parts by mass of ruthenium. When zinc is 0.1 parts by mass or more based on 100 parts by mass of ruthenium, it has high yield of cycloolefin in comparison with the case less than the amount. Furthermore, when zinc is 50 parts by mass or less, it has high activity in comparison with the case exceeding the amount.

The method for producing the ruthenium catalyst of containing ruthenium as a main component and containing the above metal and/or metal compound, includes, for example, methods of the following (1) to (4).

(1) a method in which the ruthenium compound and another metal and/or metal compound are loaded on a carrier and then subjected to reduction (2) a method in which an alkali such as sodium hydroxide is added to a solution containing the ruthenium compound and another metal and/or metal compound to precipitate the ruthenium compound together with the another metal and/or the metal compound as an insoluble salt, which is then reduced (3) a method in which an insoluble ruthenium compound is loaded on a carrier as necessary, and the ruthenium compound is reduced in a liquid phase containing another metal compound or the like (4) a method in which the ruthenium compound and another metal compound are subjected to reduction treatment in a state where they are dissolved in a liquid phase.

As described above, the ruthenium catalyst may be used by loading the ruthenium on a carrier. The carrier is not particularly limited as long as it can load general ruthenium catalysts. Specifically, the carrier includes oxides, complex oxides, hydroxides and metal salts which are not easily soluble in water, of a metal such as magnesium, aluminum, silicon, calcium, titanium, vanadium, chromium, manganese, cobalt, iron, copper, zinc, zirconium, hafnium, tungsten and boron; compounds and mixtures prepared by chemically or physically combining two or more of the above compounds.

Among them, as the carrier, zirconium oxide (zirconia) and/or zirconium hydroxide are preferred, and particularly preferred is zirconium oxide in that it has excellent physical stability of the specific surface area or the like under reaction conditions. The zirconium oxide preferably has an average particle size of from 0.05 to 30 μm, and more preferably from 0.05 to 10 μm. In order to increase catalytic activity per unit amount of ruthenium and load ruthenium in a high dispersion state, a specific surface area of zirconium oxide is preferably from 20 to 200 m$^2$/g. A method for loading ruthenium on such a carrier is not particularly limited, but includes, for example, an absorption method, an ion-exchange method, an immersion method, a coprecipitation method and solidification by drying.

Furthermore, the average particle size refers to a particle size having an accumulation of 50%, that is, an accumulation average size (center size, Median size) by measuring a particle size distribution (ratio of particles which are in a certain range of particle size) using a laser diffraction scattering particle size distribution measuring device (for example, produced by Microtrac Inc., trade name "MT-3000"), and calculating the accumulated particle size distribution based on a total volume of 100%. Furthermore, the specific surface area refers to values measured by desorption data by BET method using nitrogen gas as an adsorption gas. In the measurement of the specific surface area by BET method, for example, Micromeritics ASAP2010 produced by Shimadzu Corporation may be used.

An amount of the carrier to be used is, but is not limited to, generally from 1 to 1,000 times on a mass basis with respect to the loaded ruthenium. In particular, when zirconium oxide is used as a carrier, it is preferable to use zirconium oxide in an amount from 1 to 200 times on a mass basis with respect to the loaded ruthenium, and more preferably from 2 to 10 times. A catalyst of loading ruthenium in a high dispersion state by using zirconium oxide in an amount from 1 to 200 times on a mass basis with respect to the loaded ruthenium is preferred from the viewpoint of catalytic activity per unit amount of ruthenium.

Further, from the viewpoint of increasing selectivity of cycloolefin, it is preferred that a dispersant is present in catalyst slurry containing the ruthenium catalyst. The dispersant may be contained in the ruthenium catalyst by physical mixing, irrespective of loading or unloading. The dispersant includes, for example, oxides, complex oxides, hydroxides and metal salts which are not easily soluble in water, of a metal such as magnesium, aluminum, silicon, calcium, titanium, vanadium, chromium, manganese, cobalt, iron, copper, zinc, zirconium, hafnium, tungsten, barium and boron; compounds and mixtures prepared by chemically or physically combining two or more of the above compounds; and the like. Among them, zirconium oxide and zirconium hydroxide are preferred as the dispersant, and in particular, zirconium oxide is more preferred because it is excellent in physical stability of the specific surface area, or the like under the reaction conditions. An amount of a dispersant to be used is, but not limited to, generally from 1 to 1,000 times on a mass basis with respect to the ruthenium used as a catalyst. In particular, when zirconium oxide is used as a dispersant, it is preferably to use zirconium oxide in an amount from 1 to 200 times on a mass basis with respect to the ruthenium, and more preferably from 2 to 10 times. By using the dispersant, it can be suppressed to reduce the catalytic activity due to aggregation of the ruthenium catalyst in the reaction system. Furthermore, even when ruthenium is loaded on a carrier, the dispersant is preferably used.

The ruthenium catalyst preferably has an average crystallite size of 20 nm or less. The average crystallite size in this range is preferred because it provides a suitable surface area of the ruthenium catalyst so that the active sites are sufficiently present and the catalytic activity is improved. The average crystallite size of the ruthenium catalyst is calculated using the Scherrer equation in the light of the broadening of the diffraction line width obtained by an X-ray diffraction method of the ruthenium catalyst to be used. Specifically, the CuKα radiation is used as an X-ray source to calculate the average crystallite size in the light of the broadening of the diffraction line having a maximum near a diffraction angle (2θ) of 44°. In addition, the lower limit of the average crystallite size is theoretically larger than the crystalline unit, and it is in practice 1 nm or more.

(d) Reaction Condition

A hydrogen pressure for partially hydrogenating the monocyclic aromatic hydrocarbon with hydrogen according to the present invention is generally from 1 to 20 MPa, preferably from 2 to 7 MPa. When the hydrogen pressure is 1 MPa or more, the cycloolefin selectivity increases, and when the hydrogen pressure is 20 MPa or less, the necessity of supplying the hydrogen or the monocyclic aromatic hydrocarbons to the reactor at a high pressure is reduced, and non-effectiveness can be suppressed. A reaction temperature of the partial hydrogenation reaction is generally preferably from 50 to 250° C., and more preferably from 100 to 200° C. When the reaction temperature is 50° C. or more, the sufficient reaction velocity can be secured, and when the reaction temperature of 250° C. or less, the rapid decrease of the catalytic activity due to a growth (sintering) of the average crystallite size of the ruthenium catalyst can be suppressed.

The partial hydrogenation reaction of the monocyclic aromatic hydrocarbon is preferably a liquid phase reaction. The partial hydrogenation reaction may be typically carried out in a continuous or a batch type by a liquid phase suspension method using a reactor or two or more reactors. Instead of the liquid phase suspension method, the partial hydrogenation reaction can be carried out in a fixed-bed mode of fixing ruthenium catalyst. Examples of the methods include a method of filling a ruthenium catalyst having a size capable of being held in a fixed-bed and circulating monocyclic aromatic hydrocarbon, metal salt aqueous solution and hydrogen to the fixed-bed; and a method of circulating monocyclic aromatic hydrocarbon and hydrogen from the lower side of a fixed-bed with a ruthenium catalyst and a metal salt aqueous solution loaded to a fixed-bed.

(e) Material of Liquid-Contact Portion

When the partial hydrogenation reaction is performed over a long term, materials forming a reactor preferably do not result in hydrogen embrittlement, and have a sufficient strength under high temperature and high pressure, and corrosion-resistant materials are preferred. Materials of the reactors with these conditions include, for example, nickel-containing materials. Examples of the nickel-containing materials include a nickel group alloy containing molybdenum, a nickel group alloy containing molybdenum and chromium.

Herein, the nickel group alloy containing molybdenum is not specifically limited and includes, for example, HASTELLOY A, HASTELLOY B, HASTELLOY B-3 and HASTELLOY B-2 (trade name, heat resistance nickel alloy produced by Haynes stellite Co.). The nickel group alloy containing molybdenum and chromium is not specifically limited but includes, for example, HASTELLOY C, HASTELLOY C-276, HASTELLOY C-4, HASTELLOY C-22, HASTELLOY C-2000, HASTELLOY G, HASTELLOY G-2, HASTELLOY G-3, HASTELLOY G-30, HASTELLOY H, and HASTELLOY W (trade name, heat resistance nickel alloy produced by Haynes stellite Co.) and INCOLOY 825 (trade name, produced by Inco Alloys International, Inc.), and MAT21 (trade name, produced by Mitsubishi Materials Corporation).

Conventionally, even when a reactor formed of the nickel-containing materials as described above is used, if the partial hydrogenation reaction of monocyclic aromatic hydrocarbon is continuously performed over a long term, it has been known that a metal material constituting the liquid-contact portion of a reactor elutes and, in particular, the nickel elution content causes a remarkable decrease in the performance of ruthenium catalyst. The present inventor has been found that removal of the nickel elution content from the reaction system of the partial hydrogenation reaction, is considerably effective to stably produce cycloolefin over a long term, by using the nickel-containing material, moreover, using steps according to the present embodiment.

The steps according to the present embodiment comprise (1) a first step of bringing at least a part of the ruthenium catalyst contained in the aqueous phase into contact with oxygen, (2) a second step of separating the aqueous phase containing the ruthenium catalyst that has been processed in the first step into a first phase containing the ruthenium catalyst at a high ratio and a second phase containing the ruthenium catalyst at a lower ratio than the first phase, and (3) a third step of feeding the first phase to a reaction system of the partial hydrogenation reaction. In other words, it is one characteristic of the present embodiment that, after the ruthenium catalyst in aqueous phase containing the ruthenium catalyst is brought into contact with oxygen, at least a part of a metal salt aqueous solution in the aqueous phase containing the ruthenium catalyst is separated from most of the ruthenium catalyst, and most of the separated ruthenium catalyst is fed to the reaction system of the partial hydrogenation reaction as it is. In other words, it is one characteristic of the present embodiment that, at least a part of the metal salt aqueous solution contained in the aqueous phase after contact with oxygen is not directly fed to the reaction system of the partial hydrogenation reaction.

In a reactor of the partial hydrogenation reaction, a nickel which elutes from the nickel-containing material is mainly present on the ruthenium catalyst, and thus catalytic activity and cycloolefin selectivity are reduced. The present inventor has been founded that the aqueous phase containing the ruthenium catalyst is brought into contact with oxygen, and thereby nickel which is present on the ruthenium catalyst is desorbed from the catalyst, and is dissolved in metal salt aqueous solution. Furthermore, the aqueous phase after contact with oxygen is separated into the ruthenium catalyst and a metal salt aqueous solution dissolving nickel. The present inventor has been found that the separated ruthenium catalyst is fed to the reaction system of the partial hydrogenation reaction, and thereby a nickel concentration on ruthenium catalyst can be reduced in the reaction system of the partial hydrogenation reaction, and reduction of the catalytic performance can be suppressed.

A nickel which elutes from the nickel-containing material constituting the reactor is present on the ruthenium catalyst under a hydrogen pressing atmosphere of the partial hydrogenation reaction of the monocyclic aromatic hydrocarbon. At this time, it is thought that the nickel is reduced on the ruthenium catalyst to be present on the ruthenium catalyst in a metallic nickel state. It is thought that the ruthenium catalyst is brought into contact with oxygen, and thereby the metallic nickel is oxidized and ionized, to be dissolved in the metal salt aqueous solution where ruthenium catalyst is present.

Conventionally, in the above-described method of bringing the ruthenium catalyst into contact with oxygen in a liquid phase described above as a method of regenerating the ruthenium catalyst, the metal salt aqueous solution and the ruthenium catalyst are not separated at all after bringing a liquid phase into contact with oxygen. Accordingly, the nickel dissolved in the metal salt aqueous solution is adsorbed again on the ruthenium catalyst in the partial hydrogenation reaction, and thus the performance of ruthenium catalyst is reduced, and it is difficult to avoid the effect of catalyst poisoning due to nickel.

In the present embodiment, it is preferred to process using the each of the respective steps so as to carry out the partial hydrogenation reaction in this range where a ratio of a total mass of nickel present in the partial hydrogenation reaction to a ruthenium of a ruthenium catalyst in which a reactor accommodates does not exceed 5% by mass. The ratio of the total mass of the nickel is preferably the range of from 0.01 to 4% by mass, more preferably the range of 0.02 to 3% by mass. Herein, the total mass of nickel present in the partial hydrogenation reaction system is the sum of the total mass of nickel present on the ruthenium catalyst in a reactor and the total mass of nickel present in the metal salt aqueous solution.

The total mass of nickel on the ruthenium catalyst is derived as follows. In other words, a part of the aqueous phase containing the ruthenium catalyst in the reactor is sampled, followed by filtration and water washing. The ruthenium catalyst thus obtained is boiled in concentrated hydrochloric acid, in which nickel on the catalyst is dissolved in the concentrated hydrochloric acid. Then, a concentration of nickel in the concentrated hydrochloric acid is measured by ICP emission spectrometric analysis (ICP-AEP), and thereby the concentration of nickel on the ruthenium catalyst is calculated. The total mass of nickel on the ruthenium catalyst is derived by multiplying the obtained concentration and the amount of the ruthenium catalyst in the reactor.

Furthermore, the total mass of nickel in the metal salt aqueous solution is derived as follows. In other words, the filtrate obtained when the ruthenium catalyst is filtered, is measured by ICP emission spectrometric analysis, and thus the concentration of nickel is measured. The total mass of nickel in the metal salt aqueous solution is derived by multiplying the obtained concentration of nickel and the amount of the metal salt aqueous solution in the reactor.

The nickel which elutes from nickel-containing materials forming the hydrogenation reactor can be effectively removed from the hydrogenation reaction system by using the method of the present embodiment. As a result, reduction of the ruthenium catalyst performance due to the eluted nickel is suppressed and secure continuously stable operation becomes possible over a long term.

First Step

In a method for producing the cycloolefin of the present embodiment, a first step is a step of bringing at least a part of the ruthenium catalyst contained in the aqueous phase into contact with oxygen.

In the first step, the aqueous phase containing the ruthenium catalyst may be extracted from the reaction system (in a reactor) before bringing the ruthenium catalyst into contact with oxygen. An amount of the aqueous phase containing the ruthenium catalyst extracted from the reaction system is the whole or a part of the aqueous phase filled in the reactor. The amount of the aqueous phase may be suitably selected depending on the reaction type (batch or continuous type) of the partial hydrogenation reaction. Furthermore, in the first step, a method of bringing the ruthenium catalyst contained in the aqueous phase into contact with oxygen may be a batch type or a continuous type.

When the ruthenium catalyst is brought into contact with oxygen in the batch type, before bringing the ruthenium catalyst contained in the whole of the aqueous phase into contact with oxygen, it is preferable to recognize by a basic experiment in advance the relation between a treatment that the whole of the aqueous phase is brought into contact with oxygen, and catalytic activity and cycloolefin selectivity after the treatment. Thus, catalytic activity and cycloolefin selectivity after contact with oxygen are more easily controlled. On the other hand, the ruthenium catalyst contained in a part of the aqueous phase is brought into contact with oxygen, and thereby a part of the catalyst filled in the reactor is brought into contact with oxygen. It is thought that the following effect can be obtained by the treatment. In other words, when the treatment is performed, a catalyst of performing contact with oxygen and a catalyst of performing non-contact with oxygen are used again by mixing. Accordingly, a change in the state of the whole catalysts filled in the reactor before contact is limited to a smaller change, compared with the case where the whole catalysts contained in the aqueous phase is brought into contact with oxygen. Thus, in the partial hydrogenation reaction, catalytic activity and cycloolefin selectivity are easily optimized by controlling reaction conditions such as temperature and pressure. Therefore, at this point, the ruthenium catalyst contained in a part of the aqueous phase is preferably brought into contact with oxygen.

When cycloolefin is produced by the batch type, an amount of the aqueous phase containing the ruthenium catalyst brought into contact with oxygen is preferably 5 to 80% by mass of the aqueous phase containing the ruthenium catalyst in the reactor used in reaction, and more preferably 10 to 60% by mass. Even when the partial hydrogenation reaction is repeated, by setting the amount of the aqueous phase containing the ruthenium catalyst to the preferable range, it is easy to obtain cycloolefin stably at a high yield. Furthermore, when cycloolefin is produced by the continuous type, an amount of the aqueous phase containing the ruthenium catalyst which is brought into contact with oxygen is preferably regulated depending on the reduction of catalytic performance according to the time. For example, 5 to 80% by mass of the whole of the aqueous phase containing the ruthenium catalyst is preferably brought into contact with oxygen within 24 hours, and 10 to 60% by mass of the whole of the aqueous phase is more preferably brought into contact with oxygen within 24 hours. Thus, there is an effect where the yield of cycloolefin can be particularly improved.

When cycloolefin is produced by the partial hydrogenation reaction of the monocyclic aromatic hydrocarbon in the continuous type, the embodiments that process the first step, the second step, and the third step are not specifically limited. For example, first, continuous reaction is stopped before the first step, and the oil phase is removed from the reactor. Then, the ruthenium catalyst is brought into contact with oxygen in the state in which the whole of the aqueous phase containing the ruthenium catalyst remains in the reactor (first step). Then, the aqueous phase is separated into a first phase containing the ruthenium catalyst at a high ratio and a second phase containing (or which may not contain the ruthenium catalyst at all) the ruthenium catalyst at a lower ratio than the first phase by methods such as filtration (second step). The second phase is not filled in the reactor, the first phase, and as necessary new metal salt aqueous solution is filled in the reactor (third step). Then, the partial hydrogenation reaction is started again. Alternatively, first, continuous reaction is not stopped, and the aqueous phase containing the ruthenium catalyst is partially extracted, and the ruthenium catalyst is brought into contact with oxygen (first step). Subsequently, the aqueous phase that has been processed in the first step is separated into a first phase containing the ruthenium catalyst at a high ratio and a second phase containing (or which may not contain the ruthenium catalyst at all) the ruthenium catalyst at a lower ratio than the first phase by methods such as filtration (second step). The first phase is filled again in the reactor, and may be fed into the reaction system of the partial hydrogenation reaction (third step).

In the present embodiment, the aqueous phase containing the ruthenium catalyst before the first step is extracted from the reactor, that is, from the reaction system of the partial hydrogenation reaction. After being processed in the first step and the second step with respect to the extracted aqueous phase, the first phase is sent back to the reactor in the third step and thereby is preferably fed into the reaction system of the partial hydrogenation reaction. That is to say, after contact with oxygen, it is preferred that the second phase containing the metal salt aqueous solution is not directly sent back to the reaction system of the partial hydrogenation reaction. Thus, nickel contained in the metal salt aqueous solution in the second phase is not sent back to the reaction system, and thus reduction of catalytic performance can be reliably certainly suppressed over a long term. Herein, "not directly sent back to" means that it is not sent back to the reaction system without performing a chemical treatment in the second phase.

A trace amount of the oil phase is contained in the aqueous phase extracted from the reaction system of the partial hydrogenation reaction. In the present embodiment, the oil phase dissolved and dispersed in the aqueous phase before the first step is preferably removed from the aqueous phase. A method of removing the oil phase includes performing static separation, then blowing an inert gas such as nitrogen into the aqueous phase, and removing the oil phase contained in the aqueous phase. When the aqueous phase at the time of blowing the inert gas is heated at 50 to 90° C., a time required for removing oil phase can be reduced, and thus it is preferred.

In the first step, a state of the aqueous phase is preferably a state that the ruthenium catalyst is dispersed in the slurry-form in the metal salt aqueous solution from the viewpoint that it is suppressed that catalytic performance deteriorates because ruthenium is considerably oxidized by a rapid reaction of ruthenium in the catalyst and oxygen. The metal salt aqueous solution in the aqueous phase may be a trace amount, but it is preferred that at least the surface of the ruthenium catalyst is coated with the metal salt aqueous solution from the viewpoint that the heat of reaction of between ruthenium and oxygen is diffused and thus the rapid reaction is suppressed.

Examples of oxygen sources brought into contact with the ruthenium catalyst include a gas containing oxygen, a gas containing molecular oxygen such as air, or a compound of generating nascent oxygen such as hydrogen peroxide. The gas containing oxygen includes an oxygen gas or an oxygen gas diluted with a suitable inert gas, which is preferred from the viewpoint of simple operation.

A concentration of oxygen in the aqueous phase at the time of contact with oxygen is preferably $1 \times 10^{-7}$ to 1 NmL/mL in terms of oxygen gas in standard state, and more preferably $1 \times 10^{-5}$ to 0.1 NmL/mL. When the concentration of oxygen is in this range, a contact treating time is relatively short, and an irreversible change due to rapid oxidation can be prevented at the ruthenium on the surface of the ruthenium catalyst. Furthermore, the concentration of oxygen in the aqueous phase is measured by a commercially available oxygen meter.

The oxygen of contacting the ruthenium catalyst may be directly fed to the aqueous phase of slurry state. The most preferable method of feeding oxygen is to feed a gas containing oxygen to the aqueous phase containing the ruthenium catalyst. The method is preferred due to the simplicity of the operation.

The operation of bringing the ruthenium catalyst into contact with oxygen can be performed at any condition of reduced pressure, normal pressure and pressurization. Therefore, pressurization can be carried out for increasing the concentration of oxygen in the aqueous phase containing the ruthenium catalyst. A temperature of the aqueous phase when the aqueous phase containing the ruthenium catalyst is brought into contact with oxygen is preferably 0 to 300° C., more preferably 30 to 200° C., and still more preferably 50 to 150° C. Thus, an effect of regenerating the ruthenium catalyst due to oxygen and an effect of preventing denaturation of the ruthenium catalyst have a good balance. Furthermore, time for bringing the ruthenium catalyst into contact with oxygen may be suitably determined depending on the concentration of nickel adsorbed on the ruthenium catalyst and the amount of the targeted nickel to be removed, and is usually several minutes to several days. The nickel adsorbed on the ruthenium catalyst can be eluted in the aqueous phase by the present operation of the first step.

The present embodiment, before and after the first step, may comprise a regeneration step of maintaining the ruthenium catalyst at an atmosphere having a hydrogen partial pressure lower than that at the partial hydrogenation reaction and at a temperature not lower than the temperature lower by 50° C. than that at the partial hydrogenation reaction, which is known as a catalytic regeneration method. In the regeneration step, the ruthenium catalyst may be maintained in any of the gas phase of the atmosphere and a liquid phase encompassed by the atmosphere. The hydrogen partial pressure in the regeneration step may be lower than the hydrogen partial pressure in the partial hydrogenation reaction. However, when difference between both hydrogen partial pressures is small, a long time is required for activity restoration. Thus, the hydrogen partial pressure in the regeneration step is preferably ½ or less of the hydrogen partial pressure in the partial hydrogenation reaction, and more preferably 0 MPa. An ambient temperature of the catalyst in the regeneration step is a temperature not lower than the temperature lower by 50° C. than that at the partial hydrogenation reaction, preferably not lower than the temperature lower by 40° C. than that at the partial hydrogenation reaction, and more preferably not lower than the temperature lower by 30° C. than that at the partial hydrogenation reaction. The ambient temperature may exceed the reaction temperature, but when it is too high, since irreversible change occurs at the active site of the catalyst, it is preferred to select an upper limit of the ambient temperature suitable to the catalyst properties. For example, when a fine particle-form catalyst containing the metallic ruthenium is used as the ruthenium catalyst, it is preferred that the ambient temperature of the catalyst is not higher than 250° C., and more preferably not higher than 200° C. Thus, the physical denaturation of the ruthenium catalyst can be more efficiently prevented. On the other hand, when the ambient temperature of the catalyst is a temperature lower than the temperature lower by 50° C. than that at the partial hydrogenation reaction, there is a case where a considerably long time is required for activity restoration.

A time of maintaining the ruthenium catalyst may be suitably determined depending on activity reduction of the ruthenium catalyst to be treated or the targeted activity restoration, and is usually several minutes to several days. When the first step and the regeneration step are combined, the order of these steps is not specifically limited. However, from the viewpoint of obtaining an effect of higher activity restoration, it is preferable that the regeneration step is processed after that the first step has been processed in.

Second Step

In the second step, the aqueous phase that has been processed in the first step is separated into a first phase containing the ruthenium catalyst at a high ratio and a second phase containing the ruthenium catalyst at a lower ratio than the first phase. Herein, "containing the ruthenium catalyst at a high ratio" means that the first phase contains the ruthenium catalyst at a higher ratio than the second phase. The metal salt aqueous solution contained in the second phase may be the whole or a part of the metal salt aqueous solution contained in the aqueous phase. When the second phase is the whole of the aqueous phase, the metal salt aqueous solution that has been processed in the first step is not contained at all in the first phase. At this time, it is preferred that the second phase is not directly sent back to the reaction system of the partial hydrogenation reaction. Thus, the amount of nickel in the reaction system of the partial hydrogenation reaction can be reduced. An amount of the metal salt aqueous solution contained in the second phase may be suitably regulated according to the amount of nickel to be removed. When the elution rate of nickel based on the ruthenium catalyst is large since the liquid-contact area of the liquid-contact portion formed of nickel-containing material in the reactor is large, or when it is required that a large amount of nickel is adsorbed on the ruthenium catalyst and thus the concentration of nickel is considerably reduced, it is preferred that the amount of the metal salt aqueous solution contained in the second phase is increased. Furthermore, a method of separating the first phase from the second phase may be a batch type or a continuous type.

When cycloolefin is produced by the batch type, an amount of the metal salt aqueous solution contained in the second phase is preferably 1 to 90% by mass of the metal salt aqueous solution in the aqueous phase containing the ruthenium catalyst which is brought into contact with oxygen in the first step. The amount of the metal salt aqueous solution contained in the second phase is more preferably 5 to 80% by mass of the metal salt aqueous solution in the aqueous phase. Thus, for example, the second phase, which contains little ruthenium catalyst, can be obtained by a simple method such as static sedimentation separation, and thus it is preferred. When cycloolefin is produced by the continuous type, the amount of the metal salt aqueous solution contained in the second phase extracted from the reactor is preferably changed depending on nickel elution rate per time and concentration in the aqueous phase of the ruthenium catalyst. For example, 0.1 to 90% by mass of the metal salt aqueous solution in the aqueous phase containing the ruthenium catalyst brought into contact with oxygen within 24 hours is preferably separated as the metal salt aqueous solution contained in the second phase. The metal salt aqueous solution contained in the second phase is more preferably 1 to 70% by mass of the metal salt aqueous solution in the aqueous phase.

A method of separating the second phase containing the metal salt aqueous solution from the aqueous phase containing the ruthenium catalyst to be used includes known separation methods, for example, reduced pressure filtration, pressure filtration, centrifugal filtration, centrifugal sedimentation separation, and static sedimentation separation. Furthermore, these methods may be combined. The static sedimentation separation can be preferably used from the viewpoint that the apparatus is a relatively simple.

In the ruthenium catalyst, the amount of the adsorbed nickel is reduced by contact with oxygen in the first step. As described later in detail, after the first step, the first phase containing the ruthenium catalyst at a high ratio is directly fed to the reaction system of the partial hydrogenation reaction. Accordingly, even when the ruthenium catalyst is contained in the separated second phase, the concentration of nickel adsorbed on the ruthenium catalyst accommodated in the reactor is reduced. However, when the second phase is not fed to the reaction system of the partial hydrogenation reaction, if a large amount of the ruthenium catalyst is contained, the amount of the catalyst contributed in the partial hydrogenation reaction is reduced at that rate. Thus, it is preferred to reduce the amount of the ruthenium catalyst contained in the second phase as much as possible. When filtration is used as the separation method, the almost the entire amount of the ruthenium catalyst is collected by selecting a suitable filter, and is contained in the first phase. Furthermore, when a static separation is used as the separation method, the ruthenium catalyst is sedimented as desired by suitably selecting the static temperature and time to obtain a supernatant, the whole or a part of the supernatant is used as the second phase, whereby loss of the ruthenium catalyst can be almost removed. At this time, the static temperature is preferably 10° C. to 200° C., and more preferably 50° C. to 170° C. When the temperature is lower than 10° C., there is a tendency that the sedimentation of the ruthenium catalyst becomes slow and long time is required in separation. When the temperature is higher than 200° C., there is a tendency that the ruthenium of catalysts is denatured and catalytic performance is easily reduced in the partial hydrogenation reaction.

Third Step

In the third step, the first phase is fed to the reaction system of the partial hydrogenation reaction. At this time, the first phase is refilled to the reactor of the partial hydrogenation reaction. The refilling method may be a method of filling the first phase in the reactor in the state of stopping the partial hydrogenation reaction in the reactor and a method of filling the first phase to the reactor while performing the partial hydrogenation reaction in the reactor. A ratio of containing the ruthenium catalyst contained in the first phase is a ratio where as little as possible the ruthenium catalyst is contained in the second phase. For example, the ruthenium catalyst contained in the second phase may be 0.002 to 1% by mass based on the whole amount of the second phase.

Sixth Step

It is preferred that the method for producing cycloolefin of the present embodiment further comprises a sixth step where the metal salt aqueous solution containing the amount of nickel lower than the amount of nickel contained in the second phase is fed to the reaction system of the partial hydrogenation reaction. Examples of the method of removing the second phase from the partial hydrogenation reaction system, then feeding an aqueous solution by the amount lower than the amount of nickel contained therein include: (a) a method which comprises discarding the removed second phase, preparing a new aqueous solution by the amount lower than that of the nickel contained therein, and feeding the prepared solution to the reaction system; (b) a method which comprises reducing or removing nickel contained in the second phase, and then reusing (feeding to the reaction system) the second phase in which the nickel is reduced or removed; and (c) a method which comprises preparing a new aqueous solution by the amount lower than that of nickel contained therein and reusing (feeding to the reaction system) the second phase in which the nickel is reduced or removed.

In any case, it is preferred that the second phase is removed from the partial hydrogenation reaction system, then an aqueous solution lower than the amount of nickel contained therein is fed, and thereby the amount of nickel present in the partial hydrogenation reaction system is lower than the predetermined amount. Specifically, the amount of nickel present in the partial hydrogenation reaction system is the total mass of nickel present on the ruthenium catalyst and nickel in the metal salt-containing acidic aqueous solution. The amount is preferably 5% by mass or less and more preferably 3% by mass or less, based on the total mass of ruthenium in the ruthenium catalyst. The amount of nickel present in the partial hydrogenation reaction system is maintained in this range, and thereby the high ruthenium catalyst activity and cycloolefin selectivity are easily maintained.

The amount of nickel in the partial hydrogenation reaction system can be maintained at 5% by mass or less by controlling the amount of the separated second phase and the amount of nickel in the metal salt aqueous solution fed to a reaction system instead of the second phase. In other words, when the amount of the separated second phase is increased, and the content of nickel in the metal salt aqueous solution fed to a reaction system is reduced instead of the second phase, the amount of nickel present in the partial hydrogenation reaction system can be reduced, and the amount of nickel can be maintained at 5% by mass or less based on the total mass of ruthenium in the ruthenium catalyst. Furthermore, an amount of the separated second phase and the content of nickel in the metal salt aqueous solution fed to the reaction system instead of the second phase may be suitably selected, depending on nickel elution rate from the liquid-contact portion in the partial hydrogenation reaction and the targeted operation period. Thus, increase of the concentration of nickel in the partial hydrogenation reaction system can be suppressed. Furthermore, the nickel elution rate becomes clear by measuring the concentration of nickel in the ruthenium catalyst and the metal salt aqueous solution over time.

(a) The method of discarding the removed second phase and preparing a new aqueous solution lower than the amount of the nickel contained therein, for example, when the metal salt aqueous solution contained in the second phase is the same amount as the new metal salt aqueous solution, the concentration of nickel of the new metal salt aqueous solution may be lower than the concentration of nickel of the second phase. In particular, when the whole of the aqueous phase filled in the reactor used in the partial hydrogenation reaction is brought into contact with oxygen in the first step, most of the metal salt aqueous solution contained in the aqueous phase is separated and is contained in the second phase, a new metal salt aqueous solution is useful in order that the ruthenium catalyst is dispersed, is made to enter a slurry state, and to be used in the partial hydrogenation reaction. However, when a new metal salt aqueous solution having the low concentration of nickel is used, there is a case where the metal salt aqueous solution contained in the second phase is discarded. Since the metal salts such as zinc sulfate may be contained at a high ratio in the metal salt aqueous solution, when discarding the metal salt aqueous solution, cumbersome treatments such as neutralization, sedimentation, and separation are required.

The method of reducing the amount of nickel contained in the second phase includes a method of reducing or removing nickel in the metal salt aqueous solution contained in the second phase. Examples of the method of reducing or removing nickel in the metal salt aqueous solution contained in the second phase includes a method of bringing the second phase into contact with a metal catalyst or an ionic exchange resin and a method of precipitating and removing nickel in the metal salt aqueous solution on an electrode by electrolytic reduction. Among these methods, the method of bringing the second phase into contact with the metal catalyst is preferred from the viewpoint that nickel can be efficiently removed, and furthermore, the metal catalyst can be used repeatedly.

Furthermore, examples of the ionic exchange resin to be used include strongly acidic cation-exchange resin, weakly acidic cation-exchange resin, and chelating resin. Among them, in particular, the chelating resin is preferred since nickel can be removed from metal salt aqueous solution in a small amount. A chelating forming group of the chelating resin includes, for example, N—O base, S—N base, N—N base, O—O base, or the like. Furthermore, imino diacetic acid type [—N(CH$_2$COO$^-$)$_2$] and polyamine type [—NH(CH$_2$CH$_2$NH)$_n$—H] is available, and examples of the chelating resin having these chelating forming group are not specifically limited, but for example CR11, CR20 (produced by Mitsubishi chemical corporation) and MC-700 (produced by Sumitomo Chemtex Co., Ltd.).

Fourth Step

It is preferred that the method for producing cycloolefin of the present embodiment further comprises a fourth step of bringing the second phase into contact with a metal catalyst. Thus the nickel in the metal salt aqueous solution contained in the second phase can be reduced or removed. In this case, in the third step, the second phase that has been processed in the fourth step is fed to the reaction system of the partial hydrogenation reaction. Thus, disposal of aqueous solution containing nickel and metal salt can be prevented, and furthermore, the new metal salt aqueous solution can be reduced. Accordingly, the necessity of using a new metal salt is reduced, and the load on the environment can be reduced. The second phase containing the metal salt aqueous solution with low concentration of nickel that has been processed in the fourth step may be fed to the reaction system of the partial hydrogenation reaction at the same time with the first phase. Furthermore, the second phase containing the metal salt aqueous solution with low concentration of nickel that has been processed in the fourth step may be fed to a reaction system separately with the first phase and a uniform slurry together with the first phase may be formed in the reaction system of the partial hydrogenation reaction.

The metal catalyst contains metals as active species. Examples of the metals contained in the metal catalyst preferably include copper (Cu), silver (Ag), gold (Au), palladium (Pd), platinum (Pt), rhodium (Rh), iridium (Ir), ruthenium (Ru) and rhenium (Re). These may be used alone, or by alloys or physical mixtures of two or more of these metals. Among them, in particular, a metal catalyst containing one kind or more metals selected from the group consisting of palladium, platinum, rhodium and ruthenium, is preferred.

It is preferred that the metal catalyst contains a metal obtained by previously reducing the metal compound. The metal compound includes, for example halides such as chlorides, bromides, and iodides, or nitrates, sulfate, hydrides or various complexes (for example, carbonyl complex, acetylacetonate complex, ammine complex and hydride complex) containing the metal and a compound derived from these complexes. These metal compounds may be used alone or by mixing two or more kinds.

As methods of reducing these metal compounds, general reduction methods include, for example, a catalytic reduction method with hydrogen, carbon monoxide or the like, or a chemical reduction method with formalin, sodium borohydride, potassium borohydride, hydrazine or the like. Furthermore, the metal compounds may be one obtained by adding other metals and/or these metal compounds (for example, zinc, chromium, molybdenum, tungsten, manganese, cobalt, boron, lanthanum, cerium, and/or these metal compounds) before or after the reduction, and contained the above metals mainly.

Furthermore, the metal catalyst may be any of a catalyst consisting of only metal such as metal particles, a catalyst of mixing metal particles and dispersants, and a catalyst loading metals on a carrier.

Examples of the carriers are not specifically limited, but may include activated carbon; or oxides, complex oxides, hydroxides and metal salts, which are not easily soluble in water, of a metal such as magnesium, aluminum, silicon, calcium, titanium, vanadium, chromium, manganese, cobalt, copper, zirconium, hafnium, and tungsten; or compounds and mixtures prepared by chemically or physically combining two or more of the above compounds; and the like. Among them, one or more kind selected from the group consisting of zirconium oxide, zirconium hydroxide and activated carbon as the carrier is preferred from the viewpoint of stability with respect to acidic aqueous solution.

These carriers have an average particle size of preferably from 0.1 µm to 50 mm, more preferably from 10 µm to 10 mm from the viewpoint of separation of the acidic aqueous solution and the metal catalyst after treatment with the metal catalyst. A method for loading metal on such a carrier may be known methods and is not particularly limited, but includes, for example, an absorption method, an ion-exchange method, an immersion method, a coprecipitation method and solidification by drying.

An amount of the carrier to be used is not specifically limited, but it is preferably 1 to 1000 times on a mass basis with respect to a metal loaded there.

The dispersants include, for example, activated carbon; or oxides, complex oxides, hydroxides and metal salts, which are not easily soluble in water, of a metal such as magnesium, aluminum, silicon, calcium, titanium, vanadium, chromium, manganese, cobalt, iron, copper, zinc, zirconium, hafnium, tungsten, barium and boron; compounds and mixtures prepared by chemically or physically combining two or more of the above compounds; and the like.

The metal salt aqueous solution containing nickel in the second phase contacts the metal catalyst, and thereby the nickel in the metal salt aqueous solution is adsorbed on the metal catalyst to reduce the concentration of nickel in the metal salt aqueous solution. When the metal salt aqueous solution contacts the metal catalyst at the atmosphere containing hydrogen, an amount of nickel adsorbed per the metal catalyst is increased, and thus it is preferred.

A temperature of removing nickel from the metal salt aqueous solution containing nickel in the second phase using the metal catalyst is generally preferably 20 to 250° C., and more preferably 50 to 200° C. When the temperature is lower than 20° C., it tends to be that the amount of nickel removed is reduced. When the temperature exceeds 250° C., there is a tendency that the metal catalyst is denatured and the removing ability of nickel is remarkably reduced. A hydrogen pressure when the second phase contacts the metal catalyst under the atmosphere containing hydrogen is generally preferably 0.1 to 20 MPa, and more preferably 0.5 to 7 MPa. When the hydrogen pressure is lower than 0.1 MPa, it tends to be that the removing ability of nickel of the metal catalyst is reduced. When the hydrogen pressure exceeds 20 MPa, it is required that hydrogen or the metal salt aqueous solution fed to the reactor is used in high pressure, and thus it tends to become inefficient.

An amount of the metal catalyst to be used varies depending on the kinds of the metal catalyst, but it is in this range of generally preferably 0.01 to 100 times on a mass basis with respect to the metal salt aqueous solution contacted. A times for bringing the second phase into contact with the metal catalyst may be suitably selected from a range of several minutes to several days.

The treatment of removing nickel from the metal salt aqueous solution by placing the second phase in contact with the metal catalyst is preferably carried out in a liquid phase. The treatment can be carried out a continuous or batch type by a liquid phase suspension method using one or two or more reaction tanks. Furthermore, instead of the liquid phase suspension method, the treatment can be carried out in a fixed-bed for fixing the metal catalyst.

Fifth Step

The method for producing cycloolefin of the present embodiment preferably further comprises a fifth step where the metal catalyst that has been processed in the fourth step is brought into contact with acidic solution. Thus, the metal catalyst can be regenerated by dissolving nickel from the metal catalyst which reduces the adsorption ability of nickel that has been processed in the fourth step, in acidic aqueous solution. Examples of the acidic aqueous solutions include aqueous solution of acids such as hydrochloric acid, sulfuric acid, nitric acid, and phosphoric acid, acidic aqueous solution of the metal salt, mixtures of acidic aqueous solution of the metal salt and acids such as hydrochloric acid, sulfuric acid, nitric acid, and phosphoric acid. When the acidic solution is brought into contact with the metal catalyst that has been processed in the fourth step, nickel on the metal catalyst is dissolved in the acidic solution, then the metal catalyst is separated from the acidic solution by washing or the like, whereby the adsorption ability of nickel of the metal catalyst is restored.

When the acid is used, the concentration of the acid in the acidic solution is preferably 0.0001 to 95% by mass, and more preferably 0.005 to 10% by mass. In the case where the acid is used, when a temperature of bringing the metal catalyst into contact with the acidic solution is a low temperature, a long contact time is required, when the temperature is a high temperature, a material corrosion of the reactor due to acid may occur, thus the temperature is preferably 20 to 200° C. The contact treatment is preferably carried out in the liquid phase. Furthermore, the contact treatment may be a liquid suspension type of suspending the metal catalyst in the liquid phase or a fixed-bed type carried out by fixing the metal catalyst.

When the acidic aqueous solution of the metal salt is used as the acidic solution, examples of the metals constituting the metal salt include zinc, iron, cadmium, gallium, indium, aluminum, chromium, manganese, cobalt, and copper. Examples of the metal salts include nitrate, acetate, phosphate, sulfate, and chloride. The metal salt may be used alone or in combination with two or more kinds. Alternatively, a double salt containing such a metal salt may be used. Among them, zinc sulfate is preferred because the metal catalyst particularly has high regeneration effect. Furthermore, when the amount of the metal salt is used at low concentration, it is required to treat the metal catalyst for a long time. When the amount of the metal salt is used at high concentration, the material corrosion of the reactor may occur, and thus the concentration of the metal salt in acidic solution is preferably $1 \times 10^{-5}$ to 5.0 mol/L. When the metal salt containing zinc sulfate is used, the concentration of the metal salt in the acidic solution is more preferably $1 \times 10^{-3}$ to 2.0 mol/L and more preferably 0.1 to 1.0 mol/L.

When the metal salt acidic aqueous solution is used as the acidic solution, the metal catalyst that has been processed in the fourth step is preferably brought into contact with the acidic solution in the presence of oxygen. Thus, the metal catalyst is brought into contact with oxygen, and thus the effect of removing nickel can be further increased. At this time, the concentration of oxygen is preferably 0.1 to 20% by volume. Furthermore, the pH of the acidic aqueous solution of the metal salt may be acid, with a value of less than 7.0, and is preferably 2 to 6.5.

When the metal catalyst is brought into contact with the acidic aqueous solution of the metal salt in the presence of oxygen, regarding the system may be that the metal catalyst is a liquid phase dispersed in the acidic aqueous solution at the slurry state and the acidic aqueous solution may be a trace amount, but it is necessary that at least the surface of the metal catalyst is covered with the acidic aqueous solution.

Examples of the oxygen sources include a gas containing oxygen, a gas containing molecular oxygen such as air, or a compound of generating nascent oxygen such as hydrogen peroxide. The gas containing oxygen includes an oxygen gas or a gas that diluted an oxygen gas with a suitable inert gas, which is preferred due to the simplicity of the operation.

A concentration of oxygen in the aqueous phase is preferably $1 \times 10^{-7}$ to 1 NmL/mL in terms of oxygen gas in standard state, and more preferably $1 \times 10^{-5}$ to 0.1 NmL/mL. When the concentration of oxygen is in this range, a contact time is relatively short, and an irreversible change due to rapid oxidation is prevented at a metal on the surface of the metal catalyst. Furthermore, the concentration of oxygen in the aqueous phase is measured by a dissolved oxygen meter.

The oxygen may be directly fed to the liquid phase in the slurry state. The most preferable method of feeding the oxygen is to feed a gas containing oxygen in the liquid phase containing the metal catalyst. The method is preferred due to the simplicity of the operation.

The operation of contact with oxygen may be performed in any condition under reduced pressure, under normal pressure state or under pressurization. Therefore, pressurization can be carried out for increasing the concentration of oxygen in the liquid phase containing the metal catalyst. The operation temperature when the liquid phase containing the metal catalyst is brought into contact with oxygen is preferably 0 to 300° C., more preferably 30 to 200° C., and still more preferably 50 to 150° C. Thus, the effect of regenerating the metal catalyst due to oxygen and the effect of preventing denaturation of the metal catalyst have a good balance. Furthermore, time required in the treatment may be suitably determined depending on the concentration of nickel adsorbed on the metal catalyst and the amount of the targeted nickel to be removed, and is usually several minutes to several days.

[2] Production Apparatus of Cycloolefin

Next, description will be made with respect to a specific example of the production apparatus used in the production method of cycloolefin of the present embodiment. Therefore, the terms which are the same as the one used in the description of the production method of the cycloolefin represent the same meanings.

The production apparatus of cycloolefin of the present embodiment comprises a reactor having a liquid-contact portion formed of nickel-containing material, an oil/water separation tank connected to the reactor, an oxygen treatment equipment connected to the oil/water separation tank, and a catalyst separation tank connected to the oxygen treatment equipment. The reactor accommodates an aqueous phase which contains a metal salt-containing acidic aqueous solution and a ruthenium catalyst, a monocyclic aromatic hydrocarbon is fed thereto and a partial hydrogenation reaction of the monocyclic aromatic hydrocarbon is processed in the aqueous phase. At least a part of the reaction liquid (oil phase) containing the reaction product by the partial hydrogenation reaction and unreacted monocyclic aromatic hydrocarbon as the main component, and at least a part of the aqueous phase containing the ruthenium catalyst are fed to the oil/water separation tank in a mixed state. The oil/water separation tank is a tank to separate the reaction liquid of the oil phase from the aqueous phase. At least a part of the aqueous phase containing the ruthenium catalyst which elutes from the oil/water separation tank, is fed to the oxygen treatment equipment. The oxygen treatment equipment is an equipment to bring the ruthenium catalyst contained in the aqueous phase into contact with oxygen. The aqueous phase containing the ruthenium catalyst brought into contact with oxygen in the oxygen treatment equipment is fed to the catalyst separation tank. The catalyst separation tank is a tank to separate the aqueous phase containing the ruthenium catalyst into the first phase containing the ruthenium catalyst at a high ratio and the second phase containing the ruthenium catalyst at a lower ratio than the first phase.

FIG. 1 shows a schematic diagram illustrating a production apparatus of cycloolefin according to one example of the present embodiment. The production apparatus 100 of the cycloolefin comprises a reactor 1, an oil/water separation tank 4 attached to the reactor 1, an oxygen treatment equipment 11 connected through a pipe 9 to the oil/water separation tank 4, and a catalyst separation tank 17 connected through a pipe 16 to the oxygen treatment equipment 11.

To the reactor 1, for example, a benzene as the monocyclic aromatic hydrocarbon from a benzene feeding equipment 21 is fed through a feeding nozzle 21A, a hydrogen gas from a hydrogen feeding equipment 22 is fed through a feeding nozzle 22A, the metal salt-containing acidic aqueous solution from an acidic aqueous solution feeding equipment 23 is fed through a feeding nozzle 23A. The reactor 1 accommodates the aqueous phase containing the metal salt-containing acidic aqueous solution and the ruthenium catalyst. The partial hydrogenation reaction of the monocyclic aromatic hydrocarbon due to the hydrogen gas and benzene is progressed, while a temperature is regulated by a heating heater 2. The reactor 1 preferably comprises an inner stirrer 3 for stirring the inside thereof.

In the reactor 1, the oil/water separation tank 4 for separating a reaction liquid containing the reaction product generated by the partial hydrogenation reaction and the unreacted monocyclic aromatic hydrocarbon as the main component, in other words, the oil phase from the aqueous phase containing the ruthenium catalyst is attached. A part of the reactor 1 and the oil/water separation tank 4 is divided by a partition wall 50. Thus, the oil/water separation tank 4 is not easily affected by stirring of the stirrer 3. Furthermore, the oil phase and the aqueous phase can be moved in a mixed state to the oil/water separation tank 4 from the reactor 1 through a part which does not have the partition wall 50. In order that the oil/water separation tank 4 separates the aqueous phase from the oil phase in the predetermined time, it is preferable that it has a sufficient volume. As described above, the reaction liquid of the partial hydrogenation reaction is the oil phase which contains starting material, in other words monocyclic aromatic hydrocarbon such as benzene and a reaction product, in other words, cycloolefin as the main component. The oil phase is separated from the aqueous phase containing the ruthenium catalyst in the oil/water separation tank 4. Furthermore, in this example, the oil/water separation tank 4 is attached to the reactor 1, but the oil/water separation tank 4 may be provided outside the reactor 1, and be connected to the reactor 1 through a pipe.

The oil phase separated by the oil/water separation tank 4 is fed to a separator 6 through a pipe 8 from an overflow nozzle. The oil phase is cooled in the separator 6, to thereby separate moisture dissolved in the oil phase. The separated moisture is fed to the reactor 1 by a pump 5.

The aqueous phase separated in the oil/water separation tank 4 passes through a pipe 9 where the flow rate is controlled by a reduced pressure valve 10, and is fed to the oxygen treatment equipment 11. In the oxygen treatment equipment 11, the aqueous phase containing the ruthenium catalyst is brought into contact with oxygen, and at least a part of the ruthenium catalyst is brought into contact with oxygen. Thus, nickel present on the ruthenium catalyst is desorbed from the catalyst, to dissolve the metal salt aqueous solution in the aqueous phase. The oxygen treatment equipment 11 preferably has a stirrer 12 for stirring the aqueous phase containing the ruthenium catalyst fed thereto. Furthermore, the oxygen treatment equipment 11 is preferably covered with a heating jacket 11A so as to easily control the inner temperature. Furthermore, a production apparatus 100 has a gas feeding equipment 15 and a gas introducing nozzle 15A connecting the gas feeding equipment 15 and the oxygen treatment equipment 11, so as to introduce a gas containing oxygen of the predetermined concentration. The production apparatus 100 is preferably able to introduce a gas directly in the aqueous phase containing the ruthenium catalyst. Furthermore, to the oxygen treatment equipment 11, there may be connected a condenser 13 which condenses a part of a gas containing oxygen or the like after contact with the aqueous phase, and is sent back to the oxygen treatment equipment 11. Gas not condensed in the condenser 13 is flowed to the outside through a pipe 14.

In the oxygen treatment equipment 11, the aqueous phase containing the ruthenium catalyst brought into contact with oxygen is fed to the catalyst separation tank 17 through the pipe 16. In the catalyst separation tank 17, the aqueous phase containing the ruthenium catalyst is separated into the first phase containing the ruthenium catalyst at a high ratio and the second phase containing the ruthenium catalyst at a lower ratio than the first phase. The catalyst separation tank 17 is preferably covered with a heating jacket 17A to increase the sedimentation velocity of the ruthenium catalyst. Examples of the catalyst separation tank 17 include a separation tank of reduced pressure filtration, pressurization filtration, centrifugal filtration, centrifugal separation, or the like other than sedimentation separation type separation tank. Furthermore, the exemplified sedimentation separation type catalyst separation tank 17 preferably comprises a separation wall 52 vertically arranged from the lower side in the upstream portion, and a partition wall 53 vertically dropped from the upper side in the downstream portion. Thus, a volume which is required in separation of the ruthenium catalyst and the metal salt aqueous solution can be reduced, and hence the catalyst separation tank 17 can be made to have a small size.

The second phase separated in the catalyst separation tank 17 comprises a large amount of the metal salt aqueous solution which dissolves nickel, and the solution is discharged through a pipe 54, for example, to the outside. On the other hand, the first phase separated in the catalyst separation tank 17 comprises a low metal salt solution which dissolves nickel, and furthermore comprises a large amount of the ruthenium catalyst. The first phase is fed to the reactor 1 through a pipe 18 by a pump 19.

In the production apparatus 100 of cycloolefin, the reactor 1, the oil/water separation tank 4, the oxygen treatment equipment 11, the catalyst separation tank 17 and the pipe connected to respective equipments, are constituted by materials made of metal such as carbon steel or stainless. Furthermore, in the respective pieces of equipment, at least the liquid-contact portion with reaction liquid is preferably formed of nickel-containing materials. For example, the inner wall (inner surface) of the reactor 1 is preferably constituted by materials capable of further suppressing metal elution rate such as a nickel group alloy containing molybdenum or a nickel group alloy containing molybdenum and chromium.

Herein, the nickel group alloy containing molybdenum is not specifically limited but includes, for example, HASTELLOY A, HASTELLOY B, HASTELLOY B-3 and HASTELLOY B-2 (trade name, heat resistance nickel alloy produced by Haynes stellite Co.). The nickel group alloy containing molybdenum and chromium is not specifically limited but includes, for example HASTELLOY C, HASTELLOY C-276, HASTELLOY C-4, HASTELLOY C-22, HASTELLOY C-2000, HASTELLOY G, HASTELLOY G-2, HASTELLOY G-3, HASTELLOY G-30, HASTELLOY H, and HASTELLOY W (trade name, heat resistance nickel alloy produced by Haynes stellite Co.), or INCOLOY 825 (trade name, produced by Inco Alloys International, Inc.), MAT21 (trade name, produced by Mitsubishi Materials Corporation)

Figure 2:
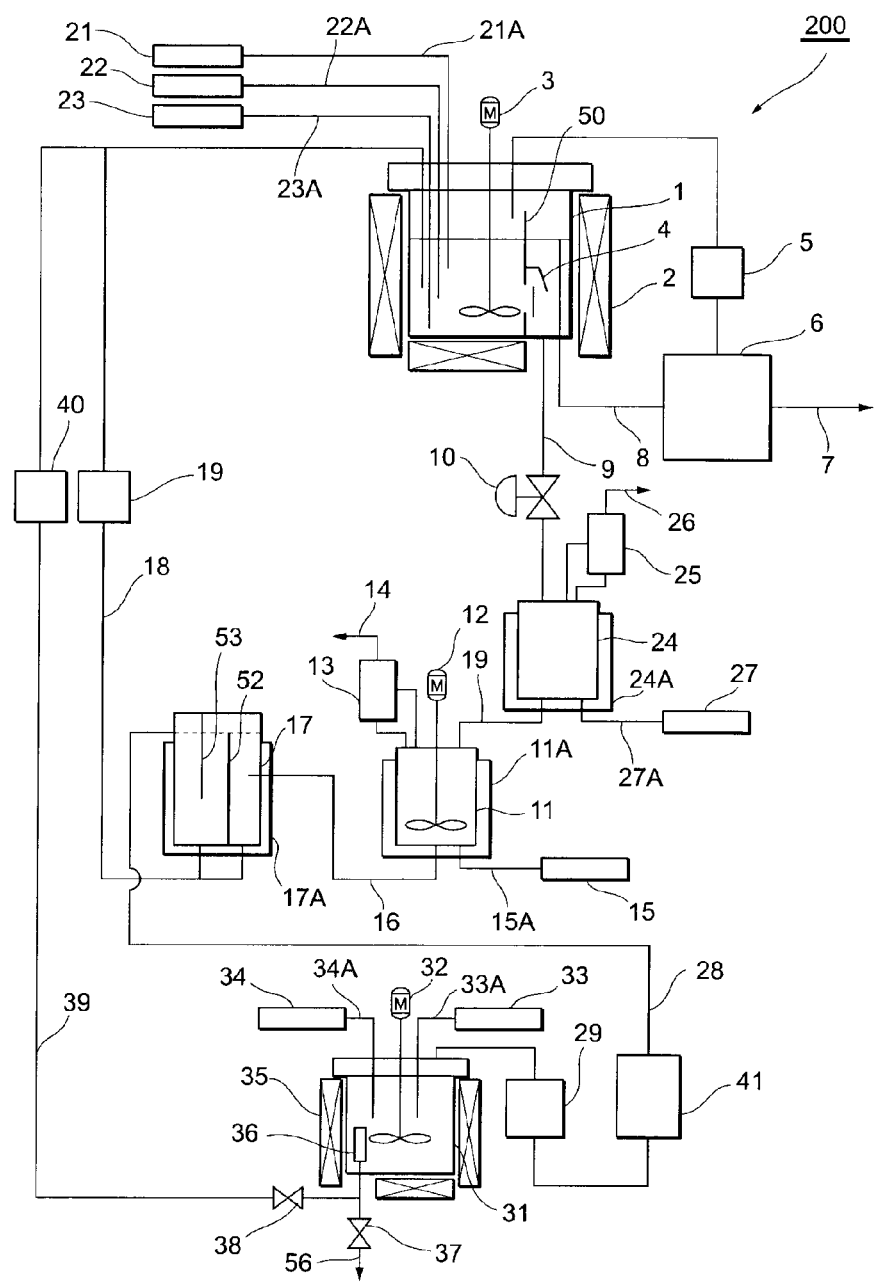
FIG. 2 shows a schematic diagram illustrating a production apparatus of cycloolefin according to another example of the invention.

FIG. 2 shows a schematic diagram illustrating a production apparatus of cycloolefin according to another one example of the present embodiment. The production apparatus 200 of cycloolefin further comprises an oil stripping tank 24 connecting between an oil/water separation tank 4 and an oxygen treatment equipment 11. Furthermore, the production apparatus 200 further has a nickel removal equipment 31 connected to the catalyst separation tank 17. Regarding elements other than the tank and equipment, the production apparatus 200 has the same elements as the production apparatus 100 shown in FIG. 1, and herein the description will be omitted. Furthermore, the oxygen treatment equipment 11 is an equipment to bring, into contact with oxygen, at least a part of the ruthenium catalyst contained in the aqueous phase that has been processed in the oil/water separation tank 4 and the oil stripping tank 24 in order and fed thereto.

The aqueous phase separated in the oil/water separation tank 4 is contained by accompanying a trace amount of the oil phase. The aqueous phase is preferably fed to the oil stripping tank 24 while the flow rate is controlled by a reduced pressure valve 10 through a pipe 9. The oil stripping tank 24 is to remove the dissolved or dispersed oil phase from the aqueous phase containing the ruthenium catalyst. In the oil stripping tank 24, an inert gas with respect to the monocyclic aromatic hydrocarbon and cycloolefin contained in the oil phase, such as nitrogen or water vapor from a gas feeding equipment 27, is blown in the aqueous phase through a gas introducing nozzle 27A. By blowing the inert gas, the oil phase containing monocyclic aromatic hydrocarbon and the partial hydrogenation reactant (cycloolefin) dissolved or dispersed in the aqueous phase as the main component is removed from the aqueous phase.

The oil stripping tank 24 is preferably covered with a heating jacket 24A so as to easily control the inner temperature. Furthermore, the condenser 25 may be connected to the oil stripping tank 24. In the condenser 25, which contains an inert gas, a volatilized oil phase, and an aqueous phase accompanied by the oil phase, the aqueous phase is condensed and is sent back to the oil stripping tank 24, and the inert gas and the volatilized oil phase is flowed to the outside through the pipe 26. The aqueous phase of removing the oil phase in the oil stripping tank 24 is fed to the oxygen treatment equipment 11 through a pipe 19.

The metal salt aqueous solution in the second phase separated by the catalyst separation tank 17 contains nickel. In the nickel removal equipment 31, the metal catalyst accommodated therein is brought into contact with the second phase, so that the nickel is adsorbed on the metal catalyst, and hence the nickel contained in the second phase is preferably reduced or removed. The second phase flowed from the catalyst separation tank 17 is fed to nickel removal equipment 31 through a pipe 28 by a pump 29. Along a pipe 28, there may be provided a buffer tank 41 for regulating the amount of the second phase fed to the nickel removal equipment 31. In the nickel removal equipment 31, the second phase is brought into contact with the metal catalyst and the nickel in the metal salt aqueous solution is removed.

In the nickel removal equipment 31, in order to carry out the treatment under the hydrogen atmosphere, it is preferred that the production apparatus 200 has a hydrogen feeding equipment 33 and a hydrogen gas is fed to the nickel removal equipment 31 through a hydrogen introducing nozzle 33A from the hydrogen feeding equipment 33. Furthermore, the nickel removal equipment 31 preferably has a stirrer 32 for stirring and mixing the second phase and the metal catalyst, and a filter 36 for filtering the metal catalyst for separating the metal catalyst from the second phase after reducing or removing nickel. In addition, the production apparatus 200 preferably has an acidic aqueous solution feeding apparatus 34. The acidic aqueous solution is fed to the nickel removal equipment 31 through an acidic aqueous solution introducing nozzle 34A from the acidic aqueous feeding apparatus 34, and thereby nickel from the metal catalyst where the nickel is adsorbed is dissolved in the acidic aqueous solution, and hence the metal catalyst can be regenerated. The nickel removal equipment 31 preferably has a heating heater 35, and thereby temperature of the nickel removal equipment 31 is easily controlled.

The nickel removal equipment 31 is connected to the reactor 1 through a pipe 39. The second phase flowed from the nickel removal equipment 31 may be flowed (discarded) to the outside through a pipe 56 in the state in which a valve 37 is opened, but is preferably fed to the reactor 1 through a pipe 39 by a pump 40 in the state which a valve 38 is opened. An example of the nickel removal equipment 31 includes a fixed-bed type treatment equipment other than the stirring and mixing tank type treatment equipment illustrated. At least a portion brought into contact with the second phase in the nickel removal equipment 31 is preferably constituted by materials capable of further suppressing a metal elution rate such as a nickel group alloy containing molybdenum or a nickel group alloy containing molybdenum and chromium as described above.

Furthermore, the production apparatuses 100 or 200 may have low hydrogen partial pressure treatment equipment (not shown) connecting between the oxygen treatment equipment 11 and the catalyst separation tank 17. The low hydrogen partial pressure treatment equipment maintains the aqueous phase containing the ruthenium catalyst fed from the oxygen treatment equipment 11 at a hydrogen partial pressure lower than that at the partial hydrogenation reaction, and at a temperature not lower than the temperature lower by 50° C. than that at the partial hydrogenation reaction, and the ruthenium catalyst contained in the aqueous phase is maintained at the temperature. Thereby, the ruthenium catalyst is regenerated. The aqueous phase maintained in low hydrogen partial pressure equipment is fed to the catalyst separation tank 17.

EXAMPLES

Hereinafter, the present invention will be described specifically by Examples and comparative Examples, but the invention is not limited to Examples so far as it does not depart from the spirit of the invention. Furthermore, the benzene conversion and cyclohexene selectivity which are shown in the following Examples were calculated by the following equations, based on concentration analytical values of benzene, cyclohexene, and cyclohexane obtained by analyzing the obtained oil phase using gas chromatography.

Benzene conversion (%)=(mole number of benzene consumed by reaction)/(mole number of benzene fed to reactor)×100   Equation 1

Cyclohexene selectivity (%)=(mole number of cyclohexene produced by reaction)/(mole number of cyclohexene produced by reaction+mole number of cyclohexane produced by reaction)×100   Equation 2

Furthermore, the concentration of the nickel in the ruthenium catalyst as the partial hydrogenation catalyst was derived by boiling the catalyst in concentrated hydrochloric acid, dissolving the nickel in the catalyst in the concentrated hydrochloric acid, and measuring the concentration of the nickel in the concentrated hydrochloric acid by ICP emission spectrometric analysis (ICP-AEP). Furthermore, the concentration of the nickel of the aqueous solution contained in the aqueous phase containing the ruthenium catalyst was also derived by measuring by ICP-AEP.

Furthermore, the metal catalyst such as 1% Pd/C used in a nickel removal treatment from the metal salt aqueous solution contained in the second phase was obtained by impregnating compounds such as nitrate and chloride of metals on a carrier according to a typical method and reducing under the hydrogen air flow.

As the carrier of the metal catalyst, powdered activated carbon having a specific surface area of 1000 m$^2$/g or powdered zirconia having a specific surface area of 80 m$^2$/g were used. These specific surface areas were measured by BET method due to nitrogen adsorption.

(1) Synthesis of Zirconia Carrier Used as Ruthenium Catalyst

While 500 g of zirconia sol containing (10% by mass of zirconia-containing liquid, trade name "ZSL-10T", produced by Daichi Kigenso Kagaku Kogyo Co., Ltd.) hafnium oxide was stirring under conditions of 40° C., 25% ammonia water was slowly added thereto. The obtained liquid was heated and stirred at 80° C. for 1 hour, followed by drying under reduced pressure at 90° C. to obtain solidified powder agglomeration. The powder agglomeration was pulverized, followed by putting in 0.5 N sodium hydroxide and stirring at 60° C. for 1 hour, and then water washing and filtration were repeated five times. The obtained solid was sufficiently subjected to vacuum drying at 110° C. and was sufficiently calcined at 400° C., to obtain 45 g of white zirconia powder. The result of the measurement of the specific surface area of the powder by BET method, it was 109 m$^2$/g.

(2) Synthesis of Ruthenium Catalyst

In an aqueous solution of dissolving 14.8 g of lanthanum acetate hydrate in distilled water, 20 g of the zirconia powder obtained as described above was added, followed by stirring and mixing for 1 hour. The obtained mixture was sufficiently subjected to drying under reduced pressure at 80° C. to obtain a solid, and subsequently the solid was sufficiently calcined at 400° C. Thus, a zirconia powder of loading 25% by mass of lanthanum in terms of oxide was obtained. Then, in an aqueous solution of adding distilled water to 22 g of aqueous ruthenium chloride solution (10% ruthenium-containing), the zirconia powder of loading lanthanum was added, followed by adsorbing and loading the ruthenium component. Then, filtration, water washing, alkali treatment at 50° C. for 1 hour, filtration, and water washing were carried out in order. 30 g of zirconia powder loading lanthanum and ruthenium thus obtained and 280 mL of 10% by mass of aqueous zinc sulfate solution were put into an autoclave, followed by stirring and reducing under conditions of hydrogen, at the condition of 150° C., total pressure of 5.5 MPa for 24 hours to obtain a ruthenium catalyst. The obtained ruthenium catalyst was analyzed by fluorescent X rays, and contained 11% by mass of ruthenium and 2% by mass of zinc. Furthermore, the ruthenium catalyst had average crystallite size of about 3 nm.

Example 1

15 g of the ruthenium catalyst prepared in above-mentioned (2) was added to 1500 mL of 11% by mass of aqueous zinc sulfate solution to prepare a slurry (hereinafter, simply referred to as "catalyst slurry") containing the ruthenium catalyst and the metal salt aqueous solution.

Reaction Experiment

A partial hydrogenation reaction of benzene was carried out by a continuous type using the known structure of a partial hydrogenation reactor in which a settling zone capable of performing oil/water separation is provided. In the reactor and the settling equipment of the inside of the reactor, a liquid-contact portion was formed of HASTELLOY C-276 (trade name, heat resistance nickel alloy produced by Haynes stellite Co) as the nickel-containing material.

The catalyst slurry was charged into the partial hydrogenation reactor described above, and the inside of the reactor was sufficiently replaced with hydrogen, and then was raised to a temperature of 140° C. Then, while a high pressure hydrogen was fed to the partial hydrogenation reactor, 1.5 kg/h of benzene was continuously fed to the partial hydrogenation reactor under high speed stirring, and simultaneously, an oil phase generated from the settling zone in the inside of the partial hydrogenation reactor was continuously extracted. Thus, cyclohexene was produced by the continuous type. The reaction temperature was set to 140° C., and the reaction pressure was set to 4.0 MPa at the total pressure. Furthermore, the settling equipment was regulated such that the ratio of oil phase/aqueous phase (catalyst slurry) in the inside of the partial hydrogenation reactor was ½. A metal salt aqueous solution having the same amount as that contained in the extracted oil phase was continuously fed to the partial hydrogen reactor.

While the partial hydrogenation reaction of benzene was continuously carried out, 700 mL of mixture of the aqueous phase and oil phase was extracted through a cooling pipe under stirring in the reactor at the same time every day. With respect to the extracted mixture, the following contact treatment with oxygen (first step), separation treatment (second step) and removal treatment (fourth step) of the nickel from the second phase were carried out to obtain reproduced catalyst slurry. The reproduced catalyst slurry was refilled into the reactor immediately after extracting the mixture the next day.

Contact Treatment with Oxygen 700 mL of mixture of the extracted aqueous phase and oil phase was separated into the oil phase and the aqueous phase by a static separation. Furthermore, the aqueous phase obtained by the separation was heated at 75° C., and bubbled with nitrogen for 1 hour. Thus, the oil was completely removed from the aqueous phase. Then, while the aqueous phase was stirred under the atmospheric pressure at 70° C., nitrogen containing 2% oxygen was blown into the aqueous phase and the aqueous phase was brought into contact with oxygen for 8 hours (first step).

Separation Treatment and Removal Treatment of Nickel from the Second Phase

The aqueous phase that had been processed in the first step containing the ruthenium catalyst was put into a reservoir, and left to stand at 80° C. for 2 hours (static separation), and the lower side of the first phase containing the ruthenium catalyst at a high ratio was separated from the upper side of supernatant (second phase) (second step). Then, 230 mL of supernatant was taken out from the reservoir. 15 g of 1% Pd/C as the metal catalyst was added to the taken supernatant, followed by stirring at 100° C., a total pressure of 4 MPa, under a hydrogen atmosphere for 2 hours, to contact the supernatant on 1% Pd/C, and then 1% Pd/C was filtered and separated from the supernatant under the nitrogen atmosphere.

Thus, the supernatant after carrying out the removal treatment of nickel was mixed with the first phase of carrying out static separation, and the obtained mixture was returned to the partial hydrogenation reactor immediately after extracting the mixture the next day (third step).

The oil phase obtained from the settling zone was sampled at 1 hour before extracting the mixture of the aqueous phase and the oil phase every day for analysis by gas chromatography, and to record the reaction result.

Thus, the partial hydrogenation reaction of benzene was carried out by a continuous type. As a result, the reaction results at 3000 hours after the reaction starting had benzene conversion of 48%, and cyclohexene selectivity of 70%. A part of the ruthenium catalyst at 3000 hours after the reaction starting was extracted, soon followed by filtering and water washing, and the concentration of nickel was analyzed, and it was 0.23% by mass. Furthermore, the concentration of nickel of the filtrate in the metal salt aqueous solution was analyzed and it was 3 ppm by mass. Accordingly, the ratio of the total mass of nickel to ruthenium in the ruthenium catalyst was 2.36% by mass.

Furthermore, reaction results when continuous reaction was continuously carried out for 6000 hours after the reaction starting, had benzene conversion of 43% and cyclohexene selectivity of 74%. The concentration of nickel in the catalyst was 0.24% by mass. Furthermore, the concentration of nickel of the filtrate in the metal salt aqueous solution was 3 ppm by mass. Accordingly, the ratio of the total mass of the nickel to the ruthenium in the ruthenium catalyst was 2.45% by mass.

Comparative Example 1

The partial hydrogenation reaction of benzene was carried out using the continuous type by the same method as Example 1, except that the aqueous phase that had been processed in the first step, which had not been processed in the second process, was directly returned to the partial hydrogenation reactor immediately after extracting the mixture the next day.

As a result, the reaction results at 3000 hours after the reaction starting had benzene conversion of 20%, and cyclohexene selectivity of 47%. The concentration of nickel in the catalyst was 0.76% by mass. The concentration of nickel of the filtrate in the metal salt aqueous solution was 4 ppm by mass. Accordingly, the ratio of the total mass of nickel to ruthenium in the ruthenium catalyst was 7.27% by mass.

Furthermore, reaction results when continuous reaction was continuously carried out for 6000 hours, had benzene conversion of 13% and cyclohexene selectivity of 29%. The concentration of nickel in the catalyst was increased to 1.52% by mass. Furthermore, the concentration of nickel of the filtrate in the metal salt aqueous solution was 4 ppm by mass. Accordingly, the ratio of the total mass of the nickel to the ruthenium in the ruthenium catalyst was 14.18% by mass.

Example 2

The aqueous phase that had been processed in the first step by the same method as Example 1 was put into a reservoir, and left to stand at 70° C. for 2 hours (static separation), and the lower side of the first phase containing the ruthenium catalyst at a high ratio was separated from and the upper side of supernatant (second phase) (second step). Then, 230 mL of the supernatant was taken out from the reservoir. Instead of the taken supernatant, an aqueous zinc sulfate solution was prepared from 51 g of new zinc sulfate heptahydrate and 230 mL of water, the prepared zinc sulfate solution was mixed with the first phase in the reservoir, and the obtained mixture was added to the partial hydrogenation reactor immediately after extracting the mixture the next day.

The oil phase obtained from the settling zone was sampled at 1 hour before extracting the mixture of the aqueous phase and the oil phase every day to analyze by gas chromatography, and to record the reaction result.

Thus, the partial hydrogenation reaction of benzene was carried out by the continuous type. As a result, the reaction results at 3000 hours after the reaction starting had benzene conversion of 48%, and cyclohexene selectivity of 70%. A part of the ruthenium catalyst at 3000 hours after the reaction starting was extracted, soon followed by filtering and water washing, and the concentration of nickel was analyzed, and it was 0.22% by mass. Furthermore, the concentration of nickel of the filtrate in the metal salt aqueous solution was analyzed and it was 3 ppm by mass. Accordingly, the ratio of the total mass of nickel to ruthenium in the ruthenium catalyst was 2.27% by mass.

Furthermore, reaction results when continuous reaction was continuously carried out for 6000 hours after the reaction starting, had benzene conversion of 45% and cyclohexene selectivity of 69%. The concentration of nickel in the catalyst was 0.24% by mass. Furthermore, the concentration of nickel of the filtrate in the metal salt aqueous solution was 3 ppm by mass. Accordingly, the ratio of the total mass of the nickel to the ruthenium in the ruthenium catalyst was 2.45% by mass.

The separated supernatant became all waste solution, and the sum of the solution at 6000 hours after the reaction starting was 57.5 L. In order to treat this as a waste, the waste solution was neutralized with sodium hydroxide and left to stand to precipitate zinc hydroxide. The supernatant generated together with the precipitation of zinc hydroxide was discarded and the precipitation was carried out by evaporation to dryness, to obtain about 4.4 kg of waste.

Example 3

After the continuous type partial hydrogenation reaction was carried out by the same method as Comparative Example 1 for 3000 hours, the reaction was stopped. Then, the whole aqueous phase (catalyst slurry) containing the ruthenium catalyst in the reactor was extracted, the aqueous phase was heated at 75° C., and bubbled with nitrogen for 1 hour. Thus, the oil was completely removed from the aqueous phase. Then, while the aqueous phase was stirred under atmospheric pressure at 70° C., nitrogen containing 2% oxygen was blown into the aqueous phase and the aqueous phase was brought into contact with oxygen for 8 hours. Then, the aqueous phase was filtered and separated into the ruthenium catalyst and aqueous zinc sulfate solution, and the ruthenium catalyst was washed with water. The concentration of nickel in the filtered and separated aqueous zinc sulfate solution was 77 ppm by mass.

50 g of 1% Pd/C as the metal catalyst was added to 500 mL of the aqueous zinc sulfate solution, followed by stirring at 150° C. and at a total pressure of 5 MPa under a hydrogen atmosphere for 3 hours, to contact the aqueous zinc sulfate solution on 1% Pd/C, then 1% Pd/C was filtered and separated from the aqueous zinc sulfate solution under the nitrogen atmosphere. Thus, the concentration of the nickel in the aqueous zinc sulfate solution after the removal treatment of nickel was less than 1 ppm.

300 mL of aqueous zinc sulfate solution after the removal treatment of the nickel and 1 g of the ruthenium catalyst prepared in above-mentioned (2) were charged into an autoclave, and was raised to a temperature of 150° C. after hydrogen substitution, and 150 mL of benzene was added thereto. Under conditions of 150° C. and 5.5 MPa, batch type partial hydrogenation reaction of benzene was carried out. As a result, benzene conversion at 30 minutes after the reaction starting was 45%. Furthermore, cyclohexene selectivity was 78% at the benzene conversion of 50%.

Comparative Example 2

By the same method as Example 3, the aqueous phase was filtered and separated into the ruthenium catalyst and aqueous zinc sulfate solution, then the ruthenium catalyst was washed with water. The concentration of the nickel in the filtered and separated aqueous zinc sulfate solution was 77 ppm.

The batch type partial hydrogenation reaction of benzene was carried out by the same method as Example 3, except that the aqueous zinc sulfate solution after the removal treatment of nickel was replaced with the aqueous zinc sulfate solution described above. As a result, benzene conversion at 30 minutes after the reaction starting was 27%. Furthermore, cyclohexene selectivity at the benzene conversion of 50% was 69%.

Example 4

The removal treatment of nickel was carried out by the same method as Example 3, except that 1% Pd/C was replaced with 2% Cu/C. The concentration of the nickel in the aqueous zinc sulfate solution after the removal treatment of nickel was 2 ppm.

Example 5

The removal treatment of nickel was carried out by the same method as Example 3, except that 1% Pd/C was replaced with 2% Ag/C. The concentration of the nickel in the aqueous zinc sulfate solution after the removal treatment of nickel was 3 ppm.

Example 6

The removal treatment of nickel was carried out by the same method as Example 3, except that 1% Pd/C was replaced with 1% Au/C. The concentration of the nickel in the aqueous zinc sulfate solution after the removal treatment of nickel was 5 ppm.

Example 7

The removal treatment of nickel was carried out by the same method as Example 3, except that 1% Pd/C was replaced with 1% Pt/C. The concentration of the nickel in the aqueous zinc sulfate solution after the removal treatment of nickel was less than 1 ppm.

Example 8

The removal treatment of nickel was carried out by the same method as Example 3, except that 1% Pd/C was replaced with 1% Rh/C. The concentration of the nickel in the aqueous zinc sulfate solution after the removal treatment of nickel was 2 ppm.

Example 9

The removal treatment of nickel was carried out by the same method as Example 3, except that 1% Pd/C was replaced with 1% Ir/C. The concentration of the nickel in the aqueous zinc sulfate solution after the removal treatment of nickel was 3 ppm.

Example 10

The removal treatment of nickel was carried out by the same method as Example 3, except that 1% Pd/C was replaced with 1% Ru/C. The concentration of the nickel in the aqueous zinc sulfate solution after the removal treatment of nickel was 1 ppm.

Example 11

By the same method as Example 3, the aqueous phase was filtered and separated into the ruthenium catalyst and aqueous zinc sulfate solution, and then the ruthenium catalyst was washed with water. The concentration of nickel of the filtered and separated aqueous zinc sulfate solution was 77 ppm.

50 g of 1% Ru/C as the metal catalyst was added to 500 mL of the aqueous zinc sulfate solution, followed by stirring at 100° C. and at a total pressure of 0.98 MPa under a hydrogen atmosphere for 3 hours, to contact the aqueous zinc sulfate solution on 1% Ru/C, then 1% Ru/C was filtered and separated from the aqueous zinc sulfate solution under the nitrogen atmosphere. Thus, the concentration of the nickel in the aqueous zinc sulfate solution after the removal treatment of nickel was 3 ppm.

Example 12

The removal treatment of nickel was carried out by the same method as Example 3, except that 1% Pd/C was replaced with 1% Ru/zirconia. The concentration of the nickel in the aqueous zinc sulfate solution after the removal treatment of nickel was 2 ppm.

Example 13

By the same method as Example 3, the aqueous phase was filtered and separated into the ruthenium catalyst and aqueous zinc sulfate solution, and then the ruthenium catalyst was washed with water. The concentration of nickel of the filtered and separated aqueous zinc sulfate solution was 77 ppm.

50 g of 1% Ru/zirconia was added to 500 mL of water, followed by stirring at 150° C., at a total pressure of 5 MPa under a hydrogen atmosphere for 3 hours, followed by filtration.

50 g of above-filtered 1% Ru/zirconia as the metal catalyst was added to 500 mL of the filtered and separated aqueous zinc sulfate solution, followed by stirring under the nitrogen atmosphere, at 140° C., for 3 hours, to contact the aqueous zinc sulfate solution on 1% Ru/zirconia, then 1% Ru/zirconia was filtered and separated from the aqueous zinc sulfate solution under the nitrogen atmosphere. Thus, the concentration of the nickel in the aqueous zinc sulfate solution after the removal treatment of nickel was 6 ppm.

Example 14

The removal treatment of nickel was carried out by the same method as Example 3, except that 1% Pd/C was replaced with 1% Re/C. The concentration of the nickel in the aqueous zinc sulfate solution after the removal treatment of nickel was 7 ppm.

Example 15

The partial hydrogenation reaction of benzene was carried out by the continuous type by the same method as Example 1, except that 1% Pd/C was replaced with 1% Ru/C as the metal catalyst. As a result, the reaction results at 3000 hours after the reaction starting had benzene conversion of 46%, and cyclohexene selectivity of 71%. A part of the ruthenium catalyst at 3000 hours after the reaction starting was extracted, soon followed by filtering and water washing, and the concentration of nickel was analyzed, and it was 0.25% by mass. Furthermore, the concentration of nickel of the filtrate in the metal salt aqueous solution was analyzed and it was 3 ppm by mass. Accordingly, the ratio of the total mass of nickel to ruthenium in the ruthenium catalyst was 2.55% by mass.

Furthermore, reaction results when continuous reaction was continuously carried out for 6000 hours after the reaction starting, had benzene conversion of 42% and cyclohexene selectivity of 75%. The concentration of nickel in the catalyst was 0.27% by mass. Furthermore, the concentration of nickel of the filtrate in the metal salt aqueous solution was 3 ppm by mass. Accordingly, the ratio of the total mass of the nickel to the ruthenium in the ruthenium catalyst was 2.73% by mass.

Example 16

1% Ru/C used in Example 10 was used again in the removal treatment of nickel in aqueous zinc sulfate solution and the concentration of nickel in aqueous zinc sulfate solution after carrying the treatment was 45 ppm. 10 g of 1% Ru/C, which was used in the above removal treatment of nickel, was added to 100 mL of 0.01N sulfuric acid, followed by stirring at the atmospheric pressure at 60° C. for 3 hours, and was washed with water until the filtrate is neutralized. The removal treatment of nickel was carried out by the same method as Example 10, except that 1% Ru/C was replaced with 1% Ru/C after the above described water washing. The concentration of the nickel in the aqueous zinc sulfate solution after the removal treatment of nickel was 1 ppm, and it was confirmed that the nickel removal ability of 1% Ru/C was restored.

INDUSTRIAL APPLICABILITY

According to the present invention, the catalyst can be maintained at high activity and high selectivity over a long term, thus the times for exchanging the catalyst is reduced and cycloolefin can be efficiently produced over a long term while reduction of cycloolefin selectivity is suppressed. Therefore, the present invention has high industrial applicability as a production method of cycloolefin.

DESCRIPTION OF REFERENCE NUMERALS

1 REACTOR
4 OIL/WATER SEPARATION TANK
11 OXYGEN TREATMENT EQUIPMENT
17 CATALYST SEPARATION TANK
24 OIL STRIPPING TANK
31 NICKEL REMOVAL EQUIPMENT

The invention claimed is:
1. A method for producing a cycloolefin, comprising:
producing the cycloolefin by a partial hydrogenation reaction of a monocyclic aromatic hydrocarbon, wherein the partial hydrogenation reaction is conducted in an aqueous phase which contains a first metal salt-containing acidic aqueous solution and a ruthenium catalyst, and wherein the partial hydrogenation reaction is conducted in a reactor with a liquid-contact portion formed of a nickel-containing material;
separating an oil phase comprising the cycloolefin and an aqueous phase containing the ruthenium catalyst and an eluted nickel; and
processing the aqueous phase containing the ruthenium catalyst and the eluted nickel through the steps including a first step of bringing at least a part of the ruthenium catalyst and the eluted nickel contained in the aqueous phase into contact with oxygen,
a second step of separating the aqueous phase containing the ruthenium catalyst and the eluted nickel that has been processed in the first step into a first phase, and a second phase, wherein the concentration of ruthenium catalyst in the first phase is higher than the concentration of ruthenium catalyst in the second phase,
a third step of feeding the first phase to a reaction system of the partial hydrogenation reaction,
a fourth step of bringing the second phase containing the ruthenium catalyst and the eluted nickel into contact with a metal catalyst to produce a second metal salt-containing acidic aqueous solution including nickel, wherein the metal catalyst contains at least one metal selected from the group consisting of Cu, Ag, Au, Pd, Pt, Rh, Ir, Ru and Re
and a fifth step of feeding the second metal salt-containing acidic aqueous solution including nickel to the reaction system of the partial hydrogenation reaction, wherein the concentration of nickel in the second metal salt-containing acidic aqueous solution is lower than the concentration of nickel in the second phase.

2. The method for producing the cycloolefin according to claim 1, wherein in the fourth step, the second phase is brought into contact with the metal catalyst under atmosphere containing hydrogen, and wherein a hydrogen pressure when the second phase contacts the metal catalyst under the atmosphere containing hydrogen is 0.1 to 20 MPa.

3. The method for producing the cycloolefin according to claim 2, further comprising a fifth step of bringing the metal catalyst that has been processed in the fourth step into contact with an acidic solution.

4. The method for producing the cycloolefin according to claim 1, wherein the metal salt contains zinc sulfate.

5. The method for producing the cycloolefin according to claim 1, wherein a sum of a total mass of nickel present on the ruthenium catalyst and a total mass of nickel in the first metal salt-containing acidic aqueous solution is controlled not to exceed 5% by mass based on a total mass of ruthenium in the ruthenium catalyst.

6. A method for producing a cycloolefin, comprising:
producing the cycloolefin by a partial hydrogenation reaction of a monocyclic aromatic hydrocarbon, wherein the partial hydrogenation reaction is conducted in an aqueous phase which contains a first metal salt-containing acidic aqueous solution and a ruthenium catalyst, and wherein the partial hydrogenation reaction is conducted in a reactor with a liquid-contact portion formed of a nickel-containing material;
separating an oil phase comprising the cycloolefin and an aqueous phase containing the ruthenium catalyst and an eluted nickel; and
processing the aqueous phase containing the ruthenium catalyst and the eluted nickel through the steps including a first step of desorbing nickel from the ruthenium catalyst by bringing at least a part of the ruthenium catalyst and the eluted nickel contained in the aqueous phase into contact with oxygen and dissolving the nickel into the aqueous phase,
a second step of separating the aqueous phase containing the ruthenium catalyst and the eluted nickel that has been processed in the first step into a first phase, and a second phase, wherein the concentration of ruthenium catalyst in the first phase is higher than the concentration of ruthenium catalyst in the second phase,
a third step of feeding the first phase to a reaction system of the partial hydrogenation reaction,
a fourth step of bringing the second phase containing the ruthenium catalyst and the eluted nickel into contact with a metal catalyst to produce a second metal salt-containing acidic aqueous solution including nickel, wherein the metal catalyst contains at least one metal selected from the group consisting of Cu, Ag, Au, Pd, Pt, Rh, Ir, Ru and Re
and a fifth step of feeding the second metal salt-containing acidic aqueous solution including nickel to the reaction system of the partial hydrogenation reaction, wherein the concentration of nickel in the second metal salt-containing acidic aqueous solution is lower than the concentration of nickel in the second phase.

* * * * *